United States Patent [19]

Kampe et al.

[11] Patent Number: 5,571,816
[45] Date of Patent: Nov. 5, 1996

[54] PYRIMIDINES

[75] Inventors: Klaus-Dieter Kampe, Bad Soden am Taunus; Ernold Granzer, Kelkheim; Michael Leineweber, Frankfurt am Main; Gerhard Rackur, Idstein/Taunus; Hans G. Böger, Hofheim am Taunus, all of Germany

[73] Assignee: Hoechst Aktiengesellschaft, Frankfurt, Germany

[21] Appl. No.: 515,882

[22] Filed: Aug. 16, 1995

Related U.S. Application Data

[63] Continuation of Ser. No. 352,745, Dec. 2, 1994, abandoned, which is a continuation of Ser. No. 17,054, Feb. 11, 1993, abandoned.

[30] Foreign Application Priority Data

Feb. 22, 1992 [DE] Germany ............... 42 05 484.2

[51] Int. Cl.⁶ ............... C07D 239/48; A61K 31/505
[52] U.S. Cl. ............... 514/275; 544/325
[58] Field of Search ............... 544/325; 514/275

[56] References Cited

U.S. PATENT DOCUMENTS

| | | | |
|---|---|---|---|
| 4,285,946 | 8/1981 | Kampe et al. | 424/251 |
| 4,705,792 | 11/1987 | Granzer et al. | 514/275 |

FOREIGN PATENT DOCUMENTS

| | | |
|---|---|---|
| 0012361 | 6/1980 | European Pat. Off. . |
| 0206297 | 12/1986 | European Pat. Off. . |

*Primary Examiner*—John M. Ford
*Attorney, Agent, or Firm*—Raymond R. Wittekind

[57] ABSTRACT

Compounds of the formula I

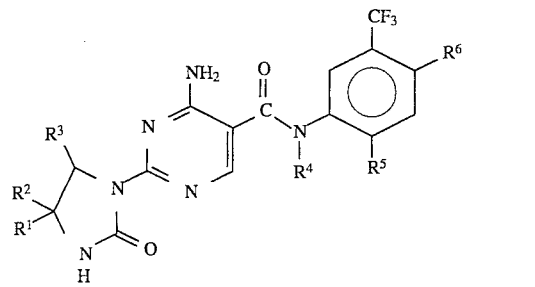

in which $R^1$ to $R^6$ have the stated meanings, and the readily water-soluble salts of these compounds, and a process for the preparation thereof are described. The compounds are suitable for the treatment of lipid metabolism disorders which are beneficially influenced by a stimulation of the hepatic LDL receptor.

Also described are compounds of the formula II

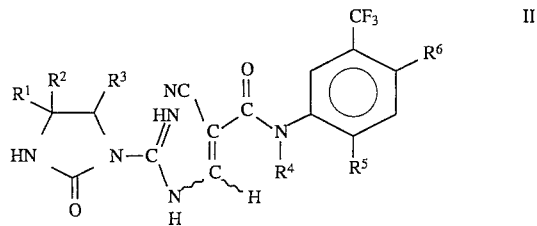

and the salts thereof.

7 Claims, No Drawings

PYRIMIDINES

This is a continuation of prior application Ser. No. 08/352,745 filed Dec. 2, 1994, now abandoned which is a continuation of application Ser. No. 08/017,054, filed Feb. 11, 1993, now abandoned.

The invention relates to tertiary amides of 4-amino-2-ureidopyrimidine-5-carboxylic acid and to the acid addition salts thereof.

In particular, the invention relates to substituted 4-amino-2-(2-oxo-1-imidazolidinyl)pyrimidine-5-carboxylic acid N-(cyclo)alkyl-N-(substituted)phenylamides and to the acid addition salts thereof.

The use of 4-amino-2-ureidopyrimidine-5-carboxylic acid N-phenylamides for the treatment of obesity and of lipid metabolism disorders has already been described [cf. Europ. Patent 0 012 361=U.S. Pat. No. 4,285,946]. The use of a group of these compounds which has a specific structure, namely corresponding N-(3-trifluoromethylphenyl)amides, for prophylaxis and treatment of thromboses has also been described [cf. Europ. Patent 0 206 297=U.S. Pat. No. 4,705,792].

However, the tolerability of the N-phenylamides proposed as pharmaceuticals, specifically of the monosubstituted secondary amides, is not entirely satisfactory. When the dosage is too high, these secondary amides inhibit to a certain degree the proliferation of some types of cells. A side effect of this type is undesirable in the use as therapeutic agents for the treatment of lipid metabolism disorders in this form.

The invention was based on the object of providing compounds which, while being well tolerated, display a therapeutically utilizable hypolipidemic effect. In this connection, the object also comprised, in particular, the finding of compounds in which, while the hypolipidemic activity is adequate, the observed antiproliferative properties are now present to only a greatly reduced extent compared with the compounds described in European Patent 0 012 361, or are entirely absent.

Another disadvantageous property of the secondary N-phenylamides which have already been proposed as pharmaceuticals and are described in European Patent 0 012 361 is regarded as being their low solubility—both as base and as acid addition salt—in water and in physiologically tolerable solvents and solvent mixtures, including mixtures of such solvents with water.

It has now been found that tertiary 4-amino-2-ureidopyrimidine-5-carboxylic acid N-phenylamides whose amide nitrogen atom is disubstituted, that is to say carries in addition to the substituted phenyl radical another radical, specifically an aliphatic or cycloaliphatic hydrocarbon radical, display a good lipid-lowering effect, while the component inhibiting the growth of certain cells, compared with the compounds mono-substituted on the amide nitrogen, is scarcely observable any longer or now observable only weakly.

The invention therefore relates to tertiary 4-amino-2-ureidopyrimidine-5-carboxamides of the formula I

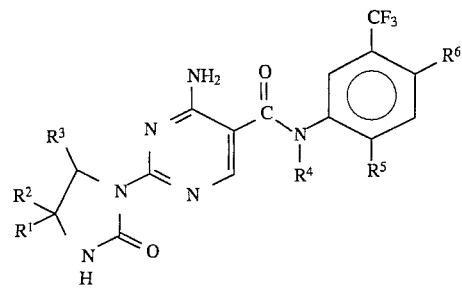

in which $R^1$ is hydrogen, $(C_1-C_4)$-alkyl, $(C_2-C_4)$-alkenyl or phenyl, $R^2$ and $R^3$ (identical or different) are hydrogen or $(C_1-C_4)$-alkyl, or $R^1$ and $R^2$ or $R^3$ and $R^2$ together are a $-(CH_2)_n-$ chain in which n is 2, 3 or 4, $R^4$ is $(C_1-C_6)$-alkyl, $(C_2-C_6)$-alkenyl, $(C_3-C_6)$-cycloalkyl, $(C_3-C_6)$-cycloalkylmethyl, 2-methoxyethyl or 2-propyn-1-yl $R^5$ is fluorine, chlorine or hydrogen and $R^6$ is fluorine, chlorine, bromine or hydrogen, and to the physiologically tolerated acid addition salts thereof, except the compounds of the following formulae A, B, C and D

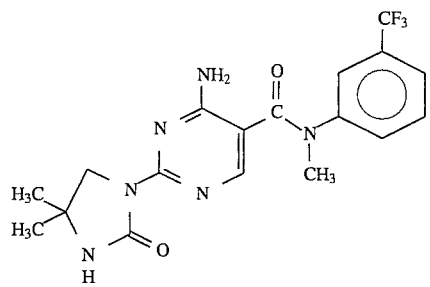

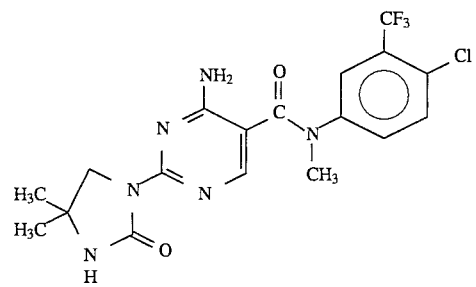

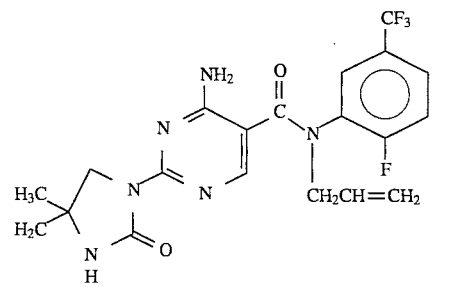

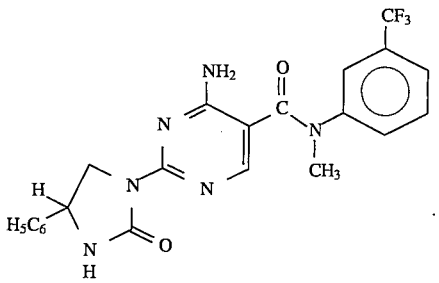

The invention also embraces—if structurally possible—the stereoisomers and—if chiral compounds exist—the optically active enantiomers.

Compounds of the formula I in which one or more of the radicals has or have the following meaning:

$R^1$ $(C_1-C_3)$-alkyl, vinyl $R^2$ $CH_3$ or $CH_5$, $R^3$ hydrogen or $CH_3$, $R_4$ $(C_1-C_4)$-alkyl, allyl, $(C_3-C_5)$-cycloalkyl or $(C_3-C_5)$-cycloalkylmethyl, $R^5$ hydrogen or fluorine, $R^6$ hydrogen, and the physiologically tolerated acid addition salts thereof, except the compounds of the formulae A and C, are preferred.

Those compounds of the formula I in which one or more of the substituents has or have the following meaning:

$R^1$ $CH_3$ $R^2$ $CH_3$ $R^3$ hydrogen $R^4$ $(C_2-C_3)$-alkyl, allyl or cyclopropylmethyl $R^5$ and $R^6$ hydrogen and the physiologically tolerated acid addition salts thereof are particularly preferred.

In the statements hereinbefore and hereinafter, the term "alkyl" means in each case an unbranched or branched alkyl radical, the term "alkenyl" means in each case an unbranched or branched alkenyl radical, and the term "$(C_3-C_5)$-and $(C_3-C_6)$-cycloalkyl" means in each case a cycloalkyl radical with a total of 3-5 and 3-6, respectively, carbon atoms, it being possible for these carbon atoms to be both members of the ring and $(C_1-C_3)$-alkyl substituents.

The nature of a selection invention is asserted for the novel compounds I in which $R^4$ is $((C_1-C_3)$-alkyl or $(C_3-C_4)$-alkenyl and which are claimed in European Patents 0 012 361 and 0 206 297 but are not described in these publications.

It has furthermore been found that tertiary 4-amino-2-ureidopyrimidine-5-carboxamides of the formula I in which $R^1-R^6$ have the abovementioned meaning are, surprisingly, readily soluble in water in the form of certain salts formed with moderately strong and strong acids. Compounds (salts) which are readily soluble in water mean compounds which are freely soluble, soluble and sparingly soluble in water according to the definition in the "Deutsches Arzneibuch" (9th edition 1986, official edition, Deutscher Apotheker-Verlag Stuttgart), page 19.

This very advantageous property, the good solubility in water of salts of the abovementioned compounds I, is exceptionally surprising because salts and the free bases of compounds which have an analogous structure but have, besides the phenyl radical, no additional hydrocarbon radical on the amide nitrogen atom are exceptionally sparingly soluble in water. Thus, for example, only a $0.93 \times 10^{-3}$ molar solution of the hydrochloride of 4-amino-2-(4,4-dimethylimidazolidin-2-on-1-yl)pyrimidine-5-carboxylic acid N-(3-trifluoromethylphenyl)amide can be prepared in water at 23° C., which means that 1 part by mass of this compound dissolves in 2500 parts of water. The compounds I in the form of the free base are, like 4-amino-2-(4,4-dimethylimidazolidin-2-on-1-yl)pyrimidine-5-carboxylic acid N-(3-trifluoromethylphenyl)amide in the form of the free base, likewise exceptionally slightly soluble in water.

Because of these properties and of the sparing solubility which is generally to be found for the compounds described in European Patent 0 012 361, both of the free bases and of the salts in water, it was by no means to be expected that salts of the compounds I are readily soluble in water.

Even the category which is designated as "sparingly soluble" according to the "Deutsches Arzneibuch" means a surprisingly large increase in the solubility in water compared with the secondary amides described in European Patent 0 012 361.

The sharp improvement in the solubility of salts of the compound I in water is also surprising because the particular structural feature of the compounds I, namely the replacement of the hydrogen atom on the amide nitrogen atom by a hydrocarbon radical with the meanings given for $R^4$, comprises the introduction of a radical which is more lipophilic than hydrogen. This exchange—of hydrogen by hydrocarbon—means that a potential hydrogen bonding disappears in the structure. The structure of the compounds I ought accordingly to become less polar. This in turn ought by no means to lead to an improvement in the solubility of the salts in water. It is known that secondary amide groups (with the structural unit HN-CO) show a great tendency to form hydrogen bonds, which as a rule lead to substances which are more polar and, as a consequence thereof, tend to be more hydrophilic. In the case of the compounds I compared with analogous compounds with a secondary amide group, surprisingly the reverse effect occurs, in that in this case substances with pronounced hydrophilicity are produced by salt formation with the compounds I containing a tertiary amide group.

The good solubility in water of salts of the compounds I has some significant advantages for the compounds I according to the invention when used as pharmaceutical. The salts of the compounds I which are readily soluble in water have, because of these properties, a beneficial effect on the absorption of these active substances by the body of the individual to be treated. Accordingly, there is also a beneficial effect on the bioavailability of the active substance in the relevant body.

The good solubility in water also has particular advantages for the pharmaceutical formulations of these active substances. It is known that active substances which form readily water-soluble salts can be pharmaceutically manipulated and processed more straightforwardly and reliably than slightly soluble or virtually water-insoluble compounds. Viewed overall, many problems relating to the formulation and the use of the compounds I as medicinal substance are simplified. Furthermore, a water-soluble medicinal substance, such as the salts of the compounds I which are readily soluble in water, is easier and safer to use, for example also with regard to dosage.

The following Table 1 lists, for the purpose of comparison, solubilities in water of salts of secondary amides with a similar structure. As is evident from Tab. 1, the listed secondary amides (Nos. 1–11) with different substitution patterns in the phenyl radical are all slightly and very slightly soluble in water, except for the compound No. 6 which is sparingly soluble in water.

Table 2 shows by way of example the solubilities of the salts, which are by contrast soluble and freely soluble in water, of the compounds I according to the invention.

TABLE 1

Solubility in water of some compounds which are described or mentioned in European Patents 0 012 361 and 0 206 297 and which are N—H analogs of the compounds I,

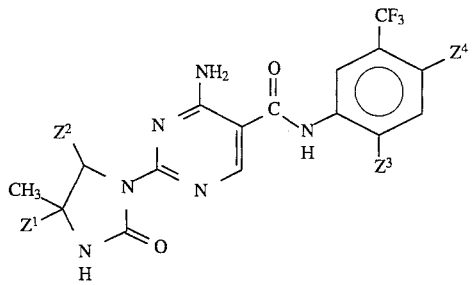

| No. | $Z^1$ | $Z^2$ | $Z^3$ | $Z^4$ | Salt | Temp. [°C.] | Molarity × $10^{-3}$ | Concentration in % by wt. | 1 part by mass dissolves in . . . parts of $H_2O$ |
|---|---|---|---|---|---|---|---|---|---|
| 1  | $CH_3$   | H      | H       | H       | * | 25.0 | 0.93  | 0.04 | 2500 |
| 2  | $CH_3$   | H      | H       | H       | # | 23.0 | 0.90  | 0.08 | 1250 |
| 3  | $CH_3$   | H      | H       | F       | * | 26.2 | 3.17  | 0.14 | 703  |
| 4  | $CH_3$   | H      | Cl      | H       | * | 25.1 | 9.91  | 0.46 | 217  |
| 5  | $CH_3$   | H      | H       | Cl      | * | 25.2 | 2.03  | 0.10 | 1055 |
| 6  | $CH_3$   | H      | $OCH_3$ | H       | * | 24.1 | 28.94 | 1.32 | 75   |
| 7  | $CH_3$   | H      | H       | $OCH_3$ | * | 24.5 | 3.92  | 0.18 | 554  |
| 8  | $C_3H_7$ | H      | Cl      | H       | * | 24.2 | 2.59  | 0.13 | 781  |
| 9  | $C_3H_7$ | H      | H       | Cl      | * | 24.2 | 2.80  | 0.13 | 725  |
| 10 | $C_3H_7$ | H      | H       | H       | * | 25.7 | 8.54  | 0.39 | 255  |
| 11 | H        | $CH_3$ | H       | H       | * | 25.8 | 8.38  | 0.36 | 277  |

\* = Hydrochloride
\# = Sulfate

TABLE 2

Solubility in water of salts of compounds I according to the invention

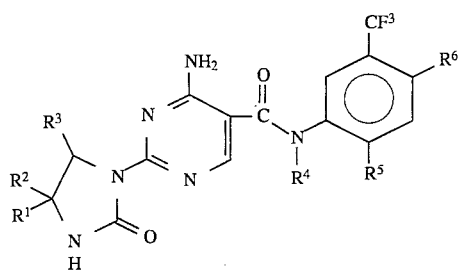

I

| No. | $R^1$ | $R^2$ | $R^3$ | $R^4$ | $R^5$ | $R^6$ | Salt | Temp. [°C.] | Concentration in % by wt. | 1 part by mass dissolves in . . . parts by $H_2O$ |
|---|---|---|---|---|---|---|---|---|---|---|
| 1 | $CH_3$ | $CH_3$ | H | $C_2H_5$ | H | H | * | 25.5 | 6.89 | 13.5 |
| 2 | $CH_3$ | $CH_3$ | H | $C_3H_7$ | H | H | * | 23.0 | 4.20 | 22.8 |
| 3 | $CH_3$ | $CH_3$ | H | $CH(CH_3)_2$ | H | H | * | 22.4 | 3.89 | 24.7 |
| 4 | $CH_3$ | $CH_3$ | H | $C_5H_{11}$ | H | H | * | 22.4 | 1.87 | 51.3 |
| 5 | $CH_3$ | $CH_3$ | H | $CH_3CHCH_2CH(CH_3)_2$ | H | H | * | 22.0 | 6.13 | 15.3 |
| 6 | $CH_3$ | $CH_3$ | H | $CH_2C(CH_3)_3$ | H | H | * | 25.0 | 1.91 | 53.3 |
| 7 | $CH_3$ | $CH_3$ | H | $CH_2CH=CH_2$ | H | H | * | 25.5 | 7.66 | 12.1 |
| 8 | $CH_3$ | $CH_3$ | H | cyclopentyl | H | H | * | 25.5 | 1.62 | 60.6 |

TABLE 2-continued

Solubility in water of salts of compounds I according to the invention

I

| No. | $R^1$ | $R^2$ | $R^3$ | $R^4$ | $R^5$ | $R^6$ | Salt | Temp. [°C.] | Concentration in % by wt. | 1 part by mass dissolves in . . . parts by $H_2O$ |
|---|---|---|---|---|---|---|---|---|---|---|
| 9 | $CH_3$ | $CH_3$ | H | $CH_2$—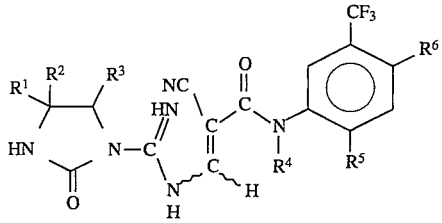 | H | H | * | 25.5 | 7.11 | 13.1 |
| 10 | $CH_3$ | $CH_3$ | H | $CH_3$ | F | H | * | 23.5 | 1.36 | 72.7 |
| 11 | $CH_3$ | $CH_3$ | H | $C_2H_5$ | F | H | * | 23.5 | 1.01 | 99.0 |
| 12 | $CH_3$ | $CH_3$ | H | $C_2H_5$ | F | H | # | 25.0 | 1.71 | 57.5 |
| 13 | $CH_3$ | $CH_3$ | H | $CH(CH_3)_2$ | H | F | * | 24.0 | 3.38 | 28.6 |
| 14 | $CH_3$ | $CH_3$ | H | $CH_2$—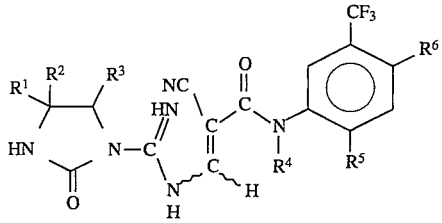 | F | H | ** | 23.0 | 1.50 | 65.8 |
| 15 | H | H | H | $CH_3$ | H | H | * | 22.0 | 4.81 | 19.8 |
| 16 | $CH_3$ | H | H | $C_2H_5$ | H | H | * | 24.5 | 12.78 | 6.8 |
| 17 | $CH_3$ | H | H | $CH_2CH(CH_3)_2$ | H | H | * | 22.5 | 3.89 | 24.7 |
| 18 | $CH=CH_2$ | H | H | $CH_3$ | H | H | * | 22.0 | >10.0 | <9 |

\* = Hydrochloride
\*\* = Hydrobromide
# = Nitrate

The invention furthermore relates to a novel process for the preparation of 4-amino-2-ureidopyrimidine-5-carboxamides of the formula I and of their salts which are readily soluble in water, which comprises cyclizing a compound of the formula II

II in which $R^1$, $R^2$, $R^3$, $R^4$, $R^5$ and $R^6$ have the meaning indicated for formula I, or a salt or a mixture of salts of a compound II at a temperature from 0° to 240° C. with or without added solvent to give a compound of the formula I or a salt or a mixture of salts of a compound I, where appropriate converting a resulting compound of the formula I into a salt which is readily soluble in water, or where appropriate converting a resulting salt or mixture of salts into a salt which is readily soluble in water.

The guanidine derivatives of the formula II are novel compounds. The invention therefore also relates to the compounds of the formula II in the form of the two possible stereoisomers, the E and the Z form, and to the acid addition salts thereof.

The invention furthermore relates to a process for the preparation of the compounds of the formula II or of the salts thereof, which comprises reacting a compound of the formula III

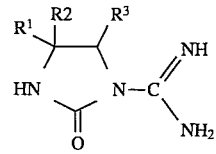

III in which $R^1$, $R^2$ and $R^3$ have the meaning indicated for formula I, or a salt of this compound III, with a compound of the formula IV

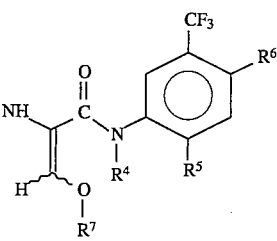

IV in which $R^4$, $R^5$ and $R^6$ have the meaning indicated for formula I, and $R^7$ is $(C_1–C_4)$-alkyl, in the presence of an organic solvent or diluent to form a compound of the formula II or a salt of this compound, and where appropriate converting the resulting compound of the formula II into a salt, or where appropriate converting a resulting salt into a compound of the formula II.

In the case where a compound III is used in the form of a salt, an, advantageously equimolar, amount of a basic compound is additionally used in the reaction with a compound of the formula III.

The compounds II are usually obtained as a mixture of stereoisomers (E and Z). They may, however, also be formed as pure stereoisomers (E or Z form). The compounds II and the salts thereof are used as starting materials for the preparation of the compounds I and of the readily water-soluble salts thereof. As monoacidic bases, the compounds II form acid addition salts. In principle, all protic acids are suitable for the formation thereof; strong to moderately strong acids are advantageously employed for the salt formation. Examples which may be mentioned are the following: hydrochloric, hydrobromic, hydrofluoric or hydroiodic acid, sulfuric, phosphoric, nitric or perchloric acid, ($C_1$–$C_4$)-alkanephosphonic acids, sulfonic acids such as methane-, benzene-, toluene- or trifluoromethanesulfonic acid, sulfamic acid, monomethyl sulfate, acetic, chloroacetic, dichloroacetic, trichloroacetic or trifluoroacetic acid, formic, propionic, oxalic, malonic, maleic, succinic, glutaric, malic, tartaric, citric, fumaric, lactic, glycolic or pyruvic acid, benzoic or benzoic acids which are substituted in the phenyl radical, such as toluylic acid or p-nitrobenzoic acid or salicylic acid, furancarboxylic and/or mandelic acid.

The compounds III which are required as starting material for the preparation of the compound II are known or can be prepared by described methods (DE-A-2,853,221).

The compounds of the formula IV can be prepared by methods which are known for this enol ether type and start from the corresponding N-cyanoacetyl-N-(cyclo)alkyl-N-(substituted)phenylamines (cf. for example, Angew. Chemie Suppl. 1982, 1213 and European Patent 0 012 361). The N-cyanoacetyl-N-(cyclo)alkyl- or -alkenyl-N-(substituted-)phenylamines required as starting materials for the preparation of the compounds IV are prepared by known methods (cf. for example, British Patent No. 930 808). The N-(cyclo)alkyl- or -alkenylanilines needed for the preparation of these cyanoacetyl compounds are known or can be obtained by known methods, such as, for example, by reductive alkylation on the aniline N or by reduction of the corresponding carboxamides with $LiAlH_4$.

A salt of a compound III means acid addition salts to be obtained with inorganic and with organic acids. Preferred salts of the compounds III are hydrobromides, hydrochlorides or sulfates. Hydrobromides and/or hydrochlorides are particularly suitable for the process according to the invention.

The reaction of an amidinoimidazolidinone of the formula III with a compound of the formula IV can take place under a wide variety of conditions. This applies both to the reaction temperature and to the solvents or diluents which are also used where appropriate. Thus, the reaction according to the invention of the compound III with a compound IV can take place at a temperature of −100° C. to +200° C. with or without the addition of a solvent or diluent. This reaction is expediently carried out at from −30° C. to +100° C., preferably from +10° C. to +35° C., in the presence of solvents or diluents.

Solvents or diluents which can be used are in principle all solvents which are (substantially) inert to the compounds III and IV, including water. Advantageously used as solvents or diluents are $C_1$–$C_5$-alcohols, tetrahydrofuran, dioxane, lower aliphatic ethers such as diethyl, methyl t-butyl and diisopropyl ethers, acetonitrile, N,N-dimethylformamide, N,N-dimethylacetamide, lower di- and monoethers of glycol and diglycol, such as 1,2-dimethoxyethane, methylglycol, ethylglycol, diglycol dimethyl and monomethyl ethers, ethyl acetate, methyl acetate, toluene, pyridine, acetone, chloroform and/or dichloromethane.

Preferred solvents and diluents are $C_2$–$C_4$-alcohols, tetrahydrofuran, dioxane, 1,2-dimethoxyethane, methyl t-butyl ether and/or acetonitrile. It is also possible to use mixtures of the solvents listed, as well as mixtures of those listed with other solvents.

It is possible in the reaction according to the invention of a compound III with a compound IV for the (stoichiometric) ratios of the amounts in which these compounds are used to vary within a wide range. III and IV can be reacted together in equivalent or in non-equivalent amounts. The latter means that one of the two compounds can be used in a stoichiometric excess. The compound III is preferably reacted as base with compound IV in equivalent amounts or in a ratio whereby the compound IV is present in a stoichiometric excess. If the compound III is used as acid addition salt, it can also be employed in a stoichiometric excess relative to IV.

The necessary reaction times depend on the temperature at which the reaction is carried out. They can vary within a wide range. As a rule, the reaction times when temperatures from +10° C. to +60° C. are used are 0.3–10 hours, with the reaction times being—as is known—inversely related to the temperature.

If the compound III is used in the form of a salt, a basic compound is added—expediently in equimolar amount—in the reaction according to the invention, or the basic compound III is, before the addition of a compound IV, partially or completely liberated from its salt with a basic compound. The basic compound which is also used for this purpose is preferably allowed to act on the salt which is used of the amidinoimidazolidinone III before addition of a compound of the formula IV. The reaction according to the invention can thus also be carried out as a "one-pot reaction" in this embodiment. Basic additives which can be used are inorganic and/or organic basic compounds. Examples which may be mentioned are: alkali metal or alkaline earth metal alcoholates of lower alcohols, alkali metal or alkaline earth metal hydroxides or hydrides, as purely organic bases tertiary a mines such as lower trialkylamines and/or N,N-dimethylaniline, diazabicycloundecene (DBU) and analogous cyclic (trisubstituted) amidines, tetraalkylammonium hydroxides, 2- or 4-dialkylaminopyridines and/or diazabicyclo[2.2.2]octane (Dabco).

Alkali metal alcoholates of ($C_1$–$C_3$)-alkanols, sodium hydride, DBU and DBU-analogous amidines or tetramethylammonium hydroxide are preferably used as basic additives, and sodium or potassium methylate and/or ethylate are particularly suitable.

An advantageous embodiment of the process according to the invention therefore comprises reacting a compound of the formula III in dissolved form at a temperature of 10° C. to 35° C. with a compound of the formula IV in which $R^5$, $R^6$ and $R^7$ have the abovementioned meaning, with $R^7$ preferably being methyl or ethyl. After a reaction time of 0.3–8 hours, the compound of the formula II which has been formed and which usually separates out as sparingly soluble crystals is isolated by filtration and dried at a temperature of 10° C. to 35° C.—expediently under vacuum.

It was surprising, knowing what is disclosed in the European Patents cited in the introduction, that on reaction of a compound III with a compound IV it is possible to isolate the particular compounds II as crystalline solid in high yields and high purity.

No compounds of the type of the compound II were observed in the preparation of the compounds described in European Patent 0 012 361. The stability of the compounds II is particularly surprising. It makes it possible conveniently to isolate these compounds, which are required as starting material for the process according to the invention, in good yields.

The isolation of the compounds of the formula II which are formed is possible with ease because of the general slight solubility of these compounds, especially in organic solvents suitable for the process according to the invention.

Since the compounds II are for the purpose of the present invention reacted to give a final product of the formula I or the readily soluble salts of these compounds I, it is not absolutely necessary to isolate the compounds II or their salts in pure form. On the contrary, the cyclization can be carried out with modification of the reaction conditions as a one-pot reaction.

The cyclization of the compounds II as base can take place with or without addition of a solvent or diluent. The cyclization in the presence of solvents or diluents is carried out at a temperature of from 0° C. to 130° C., preferably from 40° C. to 95° C. The cyclization without added solvent or diluent is carried out at a temperature from 60° C. to 240° C., preferably from 160° C. to 200° C.

If a compound II is cyclized as base to form a compound I, then one embodiment comprises heating the compound, which is expediently dried, of the formula II at a temperature of 160° C. to 200° C. for 3–27 minutes—preferably 10–20 minutes—and then immediately cooling to room temperature. The compound I which is formed from II by thermal cyclization is then isolated. This usually entails removal of two byproducts which have also been produced in trace amounts, 3-(cyclo)alkyl- or alkenylaminobenzotrifluoride (formula V in reaction scheme I) and the compound of the formula VI (cf. scheme I). The compound VI can easily be removed because of its solubility in dilute aqueous alkalis, and the compound of the formula V mostly because of its greater volatility by distillation, from the compound I. Complete removal of the compound V from the compound I is possible simply by crystallization and/or by washing the crystalline compound I with those solvents in which the compound I is slightly, and the compound V is freely, soluble.

The cyclization of a compound II in the form of an acid addition salt is preferably carried out also using solvents or diluents at a temperature from 0° C. to 150° C., preferably from 45° C. to 95° C. This cyclization of a salt of the compound II can, however, also be carried out without the addition of a solvent or diluent at a temperature from 60° C., preferably 160° C., to 240° C., preferably 200° C.

It is possible to use for this type of cyclization of the compounds II, with or without added solvent, defined acid addition salts which have been prepared separately from the compound II, as well as mixtures composed of a compound II and of one or more acids. All compositions can be used for such mixtures, starting with minimal amounts of acid equivalents, for example less than $10^{-4}$ equivalents, up to 2 acid equivalents or more; 0.8–1.6 acid equivalents are preferably used. In the extreme case, the cyclization of a compound II can be carried out in an acid which acts simultaneously as solvent or diluent. This embodiment is preferred when formic, acetic and/or propionic acid are used as acids and as diluent. Thus, it is not absolutely necessary to employ defined, separately prepared salts for the cyclization of acid addition salts of the compounds II to form a compound I.

The cyclization of a compound II with the addition of one or more acids in the presence of solvents or diluents is a very suitable embodiment of the process according to the invention.

An advantageous embodiment of the cyclization of salts of a compound II or the cyclization of a compound II with the addition of one or more acids comprises heating a compound II with the addition of 0.2 to 2.5 or more preferably 1 to 1.5—acid equivalents in the presence of a solvent or diluent at a temperature of 25° C., preferably 45° C., to 120° C., preferably 95° C. The reaction times in this case are 0.5–9 hours, depending on the temperature. It is subsequently possible, by adding suitable solvents in which the appropriate salt of the compound I which has been formed is sparingly soluble, to deposit the salt as crystals. Simple and efficient removal of a compound I which has been formed from byproducts which have also been produced is possible in this way (cf. reaction scheme I in this connection).

All protic acids can be used in principle for the carrying out which is described above of the cyclization of the compounds II. The following examples may be mentioned: hydrochloric, hydrobromic, hydrofluoric or hydroiodic acid, sulfuric, nitric or perchloric acid, $(C_1-C_4)$-alkanephosphonic acids, sulfonic acids such as methane-, benzene-, toluene- or trifluoromethanesulfonic acid, sulfamic acid, monomethyl sulfate, acetic, cyanoacetic, chloroacetic, dichloroacetic, trichloroacetic or trifluoroacetic acid, formic, propionic, oxalic, malonic, maleic, succinic, glutaric, malic, tartaric, citric, fumaric, lactic, glycolic or pyruvic acid, benzoic or benzoic acids substituted in the phenyl radical, such as toluylic acid or p-nitrobenzoic acid or salicylic acid, furancarboxylic and/or mandelic acid.

Acetic, oxalic, tartaric, formic, citric, malic, fumaric, dichloroacetic, trichloroacetic and/or propionic acid are preferably used.

Acetic, oxalic, tartaric, formic and/or citric acid are particularly suitable.

Suitable solvents or diluents for this carrying out of the cyclization of a compound II in the form of salts or salt mixtures are in principle all organic solvents which are inert to the compounds II, and/or water. Advantageously used are $C_1-C_4$-alcohols, tetrahydrofuran, dioxane, methyl t-butyl ether, acetonitrile, N,N-dimethylformamide and/or -acetamide, lower glycol di- and monoethers such as 1,2-dimethoxyethane, methyl- and/or ethylglycol, and/or methyl acetate, ethyl acetate, acetone, chloroform, dichloromethane, formic acid and/or acetic acid.

A preferred embodiment of the process according to the invention comprises heating a compound II in the presence of glacial acetic acid and/or formic acid, with or without the addition of one or more moderately strong to strong acid(s), at a temperature of 25° C., preferably 45° C., to 120° C., preferably 95° C., for 0.3 to 5 hours.

Glacial acetic acid and/or formic acid simultaneously act as solvents in this case and are used in a stoichiometric excess relative to the particular compound II. Examples of moderately strong to strong acids which are also used where appropriate and which may be mentioned are oxalic, citraconic, tartaric, citric, trifluoroacetic, cyanoacetic, chloroacetic, dichloroacetic and/or trichloroacetic acid and/or polyphosphoric acid.

If required, a compound I is liberated from the isolated salt in a manner generally known for such base formations and is converted where appropriate by the addition of an appropriate acid into a (different) salt which is soluble or readily soluble in water.

The "acid equivalents" mentioned in connection with the salt formation from compounds I relate to the compounds I as monoacidic bases.

The process according to the invention for the preparation of the compounds I is illustrated by the following scheme.

Scheme I

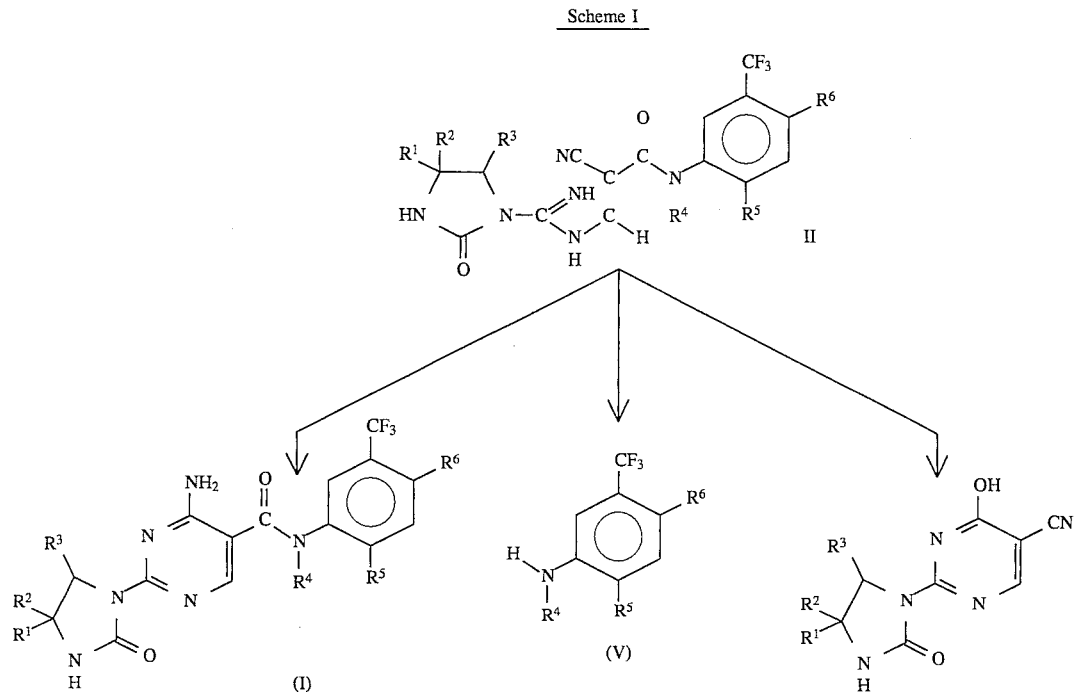

A 3-(cyclo)alkyl- or -alkenylaminobenzotrifluoride V which is formed as byproduct in the cyclization of a compound II can be isolated and returned to the process for preparing the corresponding compound IV.

The compounds of the formula I and the salts of these compounds which are readily soluble in water have valuable pharmacological properties and can therefore be used as pharmaceuticals. They are distinguished, for example, by hypolipidemic properties.

It has been found, surprisingly, that the compounds of the formula I and the salts of these compounds which are readily soluble in water increase the LDL receptor level. The compounds I and their salts which are readily soluble in water are therefore suitable for the treatment of lipid metabolism disorders which can be beneficially influenced by stimulation of the hepatic LDL receptor. The invention therefore also relates to the use of compounds I and of their salts which are readily soluble in water for the treatment of the said lipid metabolism disorders.

The effect is based on a rapid direct stimulation of the LDL receptor (apoB/E receptor) in the liver. Via stimulation of the natural cholesterol catabolism pathway, the compounds I and the salts thereof which are readily soluble in water reduce the atherogenic LDL and VLDL. The HMG-CoA reductase inhibitors or ion exchanger resins, by contrast, indirectly stimulate, owing to a reduction in the intracellular cholesterol levels or to an increase in the cholesterol required for the biosynthesis of bile acids, the expression of the LDL receptors on the liver cell. Thus, side effects like those observed with the statins owing to their drastic inhibition of HMG-CoA reductase also in organs other than the liver (for example influence on ubiquinone formation) are not to be expected. Nor have side effects of this type been observed to date. There is no risk of compliance problems like those with the ion exchanger resins which are caused by the large daily doses of 15 to 30 g required.

Particularly dangerous in atherogenesis are certain cholesterol-transporting lipoprotein fractions such as the small-particle LDL fractions. The catabolism of most of the LDL (75%) is effected by the LDL receptor in the liver. The cholesterol is then partially metabolized in the liver cells to bile acids and excreted in the form of bile, but part of the cholesterol is also directly excreted in the bile. It has thus already been recognized in principle and already demonstrated therapeutically by the substances which have an indirect effect (such as statins) that the LDL receptor is an ideal point of attack for an antiatherosclerotic with hypolipidemic activity in humans.

The compounds I and the salts thereof which are readily soluble in water increase the LDL receptor level. The increased LDL (IDL, chylomicron remnant) uptake in the liver cells, brought about by the LDL receptor level increased in this way on the cell surface, then leads to increased hepatic breakdown of LDL cholesterol. The HDL levels are unaffected.

The compounds of the formula I and the salts which are readily soluble in water thus represent an ideal principle of antiatherosclerotic activity. The following findings demonstrate the mechanism of action which has been found and which makes the described compounds appear particularly suitable for the treatment of those hyperlipidemias which are based on reduced LDL receptor activity:

1a. In the human hepatocytoma cell line HepG2, which is recognized everywhere as model, the LDL receptor mRNA levels are increased by the compounds of the formula I (Table I).

1b. The LDL receptor mRNA levels are also raised in rat livers by compounds of the formula I within a few hours (Table II).

The stimulation is in the range from 170 to 350% of the controls (control=100%).

The mRNA was prepared by the method described by Chomczynski, P. and Sacchi, N., in Anal. Biochem. 162, 156–159 (1987). In the case of organs (such as, for example, liver), the deep-frozen tissue was previously homogenized on dry ice in a mortar, and the mRNA was further concentrated by means of oligo dT by standard methods (cf. Sambrook, J., Fritsch, E. F. and Maniatis, T., Molecular Cloning, second edition, Cold Spring Harbor (1989); this collection of methods also includes descriptions of all the other relevant standard processes of molecular biology used here). 5 to 20 µm of the dissolved mRNA obtained in this way were denatured by standard processes and fractionated on 1% horizontal agarose gels. The mRNA was transferred by capillary blotting to Hybond N membranes (Amersham). Used as specific hybridization probe was a partial LDL receptor cDNA clone and as internal standard was a plasmid which contained a β-actin gene. Both plasmids were labeled using a random primer kit from Amersham to a specific activity of $5 \times 10^9$ cpm/µg. Prehybridization, hybridization and washing of the filters took place by standard processes. The filters were subsequently exposed on Cronex 4 films (Dupont) in the presence of an intensifying screen at $-70°$ C. overnight or for up to 14 days, and the hybridization signals were quantified from the intensity of blackening of the film using a commercially available laser densitometer. Subsequently, the quotient of the intensity of the LDL receptor band and of the actin band was determined as internal standard to correct for variations in yield.

Table I shows the stimulation of LDL receptor mRNA expression on HepG2 cells by selected compounds of the formula I in whole serum (final concentration of the compounds $10^{-6}$M) after incubation for 16 h. The HepG2 cells were incubated in RPMI 1640 standard medium with fetal calf serum (final concentration 10%). Serum-free RPMI medium was used as induction control. Subsequently, the complete mRNA was prepared and, by means of the Northern blot technique, the relevant LDL receptor mRNA and β-actin mRNA levels were determined. The quotient of the LDL receptor mRNA signal and of the β-actin mRNA signal of the control (without added substance) was set equal to 100%, and the stimulation above this of the LDL receptor mRNA levels achieved under the influence of the compounds was expressed as percentage of the control.

TABLE I

| Compounds of Example | Concentration | LDL receptor mRNA |
| --- | --- | --- |
| 2 | $2 \times 10^{-6}$M | 175% |
| 4 | $2 \times 10^{-6}$M | 205% |
| 8 | $2 \times 10^{-6}$M | 237% |
| 12 | $2 \times 10^{-6}$M | 170% |
| 33 | $2 \times 10^{-6}$M | 205% |
| 40 | $2 \times 10^{-6}$M | 180% |
| 42 | $2 \times 10^{-6}$M | 180% |

Table II shows the stimulation of LDL receptor mRNA expression in rat livers 6 hours after administration of selected compounds of the formula I (dose of 30 mg/kg). Liver tissue was removed and shock-frozen in liquid nitrogen.

Subsequently, the mRNA was isolated as described and, by means of the Northern blot technique, the relative LDL receptor mRNA levels were determined. The mRNA level of untreated control animals was set equal to 100%, and the stimulation of the LDL receptor mRNA was calculated as a percentage of the

TABLE II

| Compounds of Example | Concentration | LDL receptor mRNA |
| --- | --- | --- |
| 2 | 30 mg/kg | 300% |
| 4 | 30 mg/kg | 221% |
| 33 | 30 mg/kg | 350% |
| 40 | 30 mg/kg | 340% |
| 42 | 30 mg/kg | 312% |

2. In the HMG-CoA reductase determination in vitro on partially purified HMG-CoA reductase from rat liver (cf. Avigan J., Bathena, S. J., and Schreiner, M. E., J. Lipid Res. 16, 151 (1975) and Philippi, B. W., and Shapiro, D. J., J. Lipid Res. 20, 588 (1979)), the hydrochlorides of compounds I on addition of $10^{-5}$ do not influence M (final concentration), the enzyme activity compared with control incubations (variation 10%), while lovastatin Na (with opened lactone ring) has an $IC_{50}$ of $3 \times 10^{-9}$M in this experiment.

3. In vivo, the increased LDL receptor activity in experimental animals is reflected by reduction in the lipoprotein fractions which can be metabolized by the LDL receptor (apoB/E receptor), i.e. a reduction in the LDL and VLDL levels is observed. The following test was carried out:

Effect on serum lipoproteins of normolipemic male rats in a subchronic experiment Groups of in each case 10 male rats of the HOE: WISKf (SPF 71) strain with an initial weight above 180 g received once a day (in the morning) the test product or the comparison product in 1% aqueous ®Tylose MH 300 solution by stomach tube (0.5 ml/100 g of body weight); the control group in each case received only the vehicle. The last (7th) administration took place 24 hours before removal of blood and sacrifice. There was free access to food and water during the test. The food was withdrawn 24 hours before the removal of blood.

The serum from all 10 rats in a group was pooled for the analysis of the serum lipoproteins. The serum lipoproteins were separated with a preparative ultracentrifuge (KONTRON TGA 65, Rotor BECKMAN 50.4 Ti).

The following conditions specified by Koga, S., Horwitz, D. L., and Scanu, A. M., Journal of Lipid Research 10, 577 (1969) and Havel, R. J., Eder, H. A., and Bragdon, H. H., J. Clin. Invest. 34, 1345 (1955) were used to separate VLDL and LDL: 1. VLDL: Density<1.006, 40,000 rpm for 16 hours 2. LDL: Density 1.006–1.04, 40,000 rmp for 16 hours Test kits from BOEHRINGER/Mannheim were used for the enzymatic determination of cholesterol and triglycerides in the separated lipoprotein fractions (cf. Siedel, J., Schlumberger, H., Klose, S., Ziegenhorn, J. and Wahlefeld, A. W., J. Clin. Chem. Clin. Biochem. 19, 838 (1981) and Wahlefeld, A. W., in: H. O. Bergmeier: Methoden der enzymatischen Analyse (Methods of Enzymatic Analysis), 2nd edition, Volume II, Verlag Chemie 1974, page 1878). The proteins were determined by the method of Lowry (Lowry, O. H., Roseborough, N. H., Farr, A. L. and Randell, R. J., J. Biol. Chem. 193, 265 (1951)).

The results are compiled in Table III. Clofibrate was used as comparison product.

TABLE III

| Compound of Example | Dose mg/ kg/ day | Serum % change from control at end of treatment | | | | |
|---|---|---|---|---|---|---|
| | | Cholesterol | | Protein | | Triglycerides |
| | | VLDL | LDL | VLDL | LDL | VLDL |
| 2 | 30 | −96 | −75 | 40 | −73 | −81 |
|   | 10 | −41 | −32 | −28 | −28 | −26 |
|   | 3  | −30 | 40  | −7  | −28 | 40  |
|   | 1  | −22 | −28 |     | −44 |     |
| 4 | 30 | −70 | −68 | −13 | −53 | −29 |
|   | 10 | +2  | −39 | −18 | −33 |     |
| 6 | 30 | 41  | −62 | −41 | −36 | −69 |
|   | 10 | −35 | −20 | −15 | −62 |     |
|   | 3  | −35 | −24 | −12 | −3  |     |
| 8 | 30 | −39 | −30 | −26 | −18 | −37 |
| 12| 30 | −80 | −66 | −51 | −30 | −29 |
|   | 10 | −63 | 46  | −34 | −18 | −51 |
|   | 3  | −6  | −26 | −8  | −5  | −4  |
| 28| 30 | −79 | −75 | −49 | −62 | −56 |
|   | 10 | −74 | −33 | 41  | −68 | 46  |
|   | 3  | −2  | +1  | −29 | −26 |     |
| 29| 30 | −80 | −51 | 40  | −27 | −70 |
| 30| 10 | −29 | −25 | −36 | −19 | +7  |
| 32| 30 | −100| −76 | −39 | −49 | −80 |
|   | 10 | −85 | −54 | −73 | −36 | −68 |
| 33| 30 | −95 | −67 | −33 | 44  | −100|
|   | 10 | 48  | −47 | −29 | −33 | −73 |
| 35| 30 | −79 | 46  | −69 | −35 | −55 |
| 36| 30 | −65 | −38 | −33 | −5  | 42  |
| 37| 30 | −85 | −76 | −48 | −49 | −75 |
|   | 10 | −56 | −39 | −30 | −21 | −40 |
| 40| 30 | −57 | −58 | −52 | −52 | −41 |
|   | 10 | −40 | −53 | −41 | −38 | −2  |
|   | 3  | −19 | −22 | −11 | −18 |     |
| 41| 30 | −100| −66 | −45 | −36 | −80 |
|   | 10 | −100| −73 | −52 | −48 | −68 |
| 42| 30 | −70 | −48 | −40 | −29 | −61 |
|   | 10 | −23 | −29 | −10 | −9  | −29 |
|   | 3  | −23 | −34 | −11 | −22 | −29 |
| 55| 30 | −14 | −29 | −18 | −9  | −20 |
| 58| 30 | −59 | 46  | −22 | −25 | −40 |
| 64| 30 | −18 | −20 | −28 | −10 |     |
| Clofibrate | 100 | −51 | −31 | −30 | −3 | −34 |

4. Comparative antiproliferative investigations: Exponentially growing tumor cells (mouse leukemia cells, L1210; bronchial carcinoma cells, A549; colon carcinoma cells, HT29) are inoculated in a concentration of $5 \times 10^3$ cells per ml in RPMI standard medium in 96-well microtiter plates. Serial concentrations of test substance were incubated at 37° C., 5% $CO_2$, 95% relative humidity for 72 hours. Each concentration of compound or control is tested in four parallel incubations in this case. After 65 hours, 50 μl of MTT [3-(4,5-dimethyl-2-thiazolyl)-2,5-diphenyl-2H-tetrazolium bromide] in 2.5 mg/ml PBS are added. In intact cells, MTT is reduced to a red insoluble dye. After incubation for a further 7 to 24 hours, depending on the cell line used, the supernatant is removed. The resulting insoluble dye is dissolved in 100 μl of DMSO by shaking cautiously, and the extinction at 492 nm is measured in a Multiscan 340 CC photometer from Flow.

The results are calculated as quotients of the mean values of the extinctions for the test substances and the control values. The variations in the individual values determined within the parallel values are less than 15%. The $IC_{50}$ for the given compounds is read off dose-effect plots.

The compounds of the formula I can be used as pharmaceuticals in the form of their pharmaceutically acceptable acid addition salts—this use form is preferred—or as free base because of their pharmacological properties, and they are administered either alone or mixed with suitable excipients and/or compatible diluents and, where appropriate, also with other additives too.

The present invention also relates to pharmaceutical compositions which, besides non-toxic, inert pharmaceutically suitable excipients, contain one or more active substances according to the invention or which are composed of the active substances according to the invention, and to processes for the production of these compositions.

Non-toxic, inert pharmaceutically suitable excipients mean pharmaceutically acceptable, solid, semisolid or liquid diluents, fillers and formulation aids of every type which, after mixing with the active substance, convert it into a form suitable for administration.

Examples of suitable administration forms of the compounds according to the invention are tablets, coated tablets, capsules, pills, aqueous solutions, suspensions and emulsions, where appropriate sterile injectable solutions, non-aqueous emulsions, suspensions and solutions, sprays and formulations with protracted release of active substance.

The therapeutically effective compounds should be present in the abovementioned pharmaceutical compositions expediently in a concentration of about 0.1, preferably of 0.5, to 99.0, preferably to 70.0, percent by weight of the complete mixture.

The administration concentrations for solutions and aerosols in the form of spray are generally from 0.1 to 20, preferably 0.5–5, percent by weight.

The abovementioned pharmaceutical compositions may, apart from the active substances according to the invention, also contain other pharmaceutical active substances.

The abovementioned pharmaceutical compositions are produced in a conventional way by known methods, for example by mixing the active substance or substances with the excipient or excipients. Suitable tablet compositions are described in the Examples (118 and 119).

The present invention also relates to the use of active substances according to the invention and of pharmaceutical compositions which contain one or more of the active substance(s) according to the invention in human medicine to prevent, improve and/or cure the abovementioned disorders.

The active substances or the pharmaceutical compositions can be administered orally, parenterally, intraperitoneally and/or rectally.

The compounds of the present invention which can be used, for example, as hypolipidemic—preferably its salts—can be used to produce pharmaceutical products which contain an effective amount of the active substance together with excipients and which are suitable for enteral and parenteral administration. Preferably used are tablets or capsules (gelatin capsules) which contain the active substance together with diluents or excipients, for example lactose, dextrose, sucrose, mannitol, sorbitol, cellulose, various types of starch and/or glycine, and lubricants such as diatomaceous earth, talc, stearic acid or the salts thereof, such as magnesium or calcium stearate, and/or polyethylene glycol. Tablets also contain binders such as magnesium carbonate, magnesium aluminum silicate, starch, gelatin, tragacanth or methylcellulose, sodium carboxymethylcellulose and/or polyvinylpyrrolidone and, if necessary, colorants, flavorings and sweeteners. Injectable solutions are preferably isotonic aqueous solutions or suspensions which can be sterilized and can contain ancillary substances such as preservatives, stabilizers, wetting agents and/or emulsifiers, solubilizers, salts to regulate the osmotic pressure and/or buffer substances. The pharmaceutical products according to the invention, which can optionally contain further pharmacologically active substances, are produced, for example, by conventional mixing, granulating and coating processes and contain 0.1% to, preferably, 80%, preferably about 0.5% to about 65% of the active substance.

Oral administration takes place in pharmaceutically customary compositions, for example in the form of tablets, coated tablets or capsules which, for example, contain per daily dose 5, preferably 20, to 1000 mg, preferably to 200 mg, of the active substance mixed with a conventional excipient and/or constituent, it being possible to give single doses of 5 to 200 mg, preferably once to three times a day.

However, it may be necessary to deviate from the said dosages, specifically depending on the nature and the body weight of the subject to be treated, the nature and the severity of the disorder, the nature of the composition and of the administration of the pharmaceutical, as well as the period or interval over which administration takes place. Thus, it may be sufficient in some cases to make do with less than the abovementioned amount of active substance, whereas in other cases the abovementioned amount of active substance must be exceeded. Establishment of the optimal dosage and mode of administration of the active substances necessary in each case can easily be carried out by any skilled worker on the basis of his expert knowledge.

The following examples serve to illustrate the invention further but without confining the latter to the products and embodiments described in the examples.

The temperatures are stated in °C.

The melting and decomposition points stated in the following examples are uncorrected.

Thin-layer chromatographies were carried out on precoated silica gel 60, F-254 TLC plates from Riedel-de-Haen AG, with the mobile phase $CH_2Cl_2/C_2H_5OH$ 10:1 (v/v) unless another mobile phase is stated in the examples.

EXAMPLE 1

A suspension of 1.267 g (3 mmol) of a compound II in which $R^1$ and $R^2$ are $CH_3$, $R^3$, $R^5$ and $R^6$ are hydrogen and $R^4$ is $C_2H_5$ in 3 ml of glacial acetic acid was stirred at 50° for 5 hours and subsequently evaporated in vacuo. The remaining residue was taken up in $H_2O/CH_2Cl_2$. The aqueous phase was adjusted to pH 9 with 2N NaOH. After phase separation, the aqueous phase was extracted twice with $CH_2Cl_2$. The combined $CH_2Cl_2$ extracts were washed with $H_2O$, dried over $MgSO_4$, filtered and evaporated in vacuo. The residue (1.07 g) was dissolved in ether, whereupon crystallization took place. The mass of crystals was filtered off with suction, washed with ether and dried at 100° in vacuo (6 mbar) for 15 hours. 0.86 g (67.9% yield) of TLC-pure 4-amino-2-(4,4-dimethyl-2-oxo-1-imidazo-lidinyl)pyrimidine-5-carboxylic acid N-ethyl-N-(3-trifluoromethylphenyl)amide was obtained, melting point 186°–187°.

$C_{19}H_{21}F_3N_6O_2$ (422.43) Calculated: C 54.02 H 5.01 F 13.49 N 19.90% Found: C 53.5 H 5.2 F 12.9 N 19.7%

EXAMPLE 2

1.52 ml of a 6.6 molar solution of HCl in ether were added dropwise to a solution of 3.80 g (9 mmol) of 4-amino-2-(4, 4-dimethyl-2-oxo-1-imidazolidinyl)-pyrimidine-5-carboxylic acid N-ethyl-N-(3-trifluoromethylphenyl)amide prepared as in Example 1 in 20 ml of acetone at room temperature, and the resulting suspension was stirred while cooling in ice for 20 minutes. The crystals were then filtered off with suction, washed with acetone and ether and dried in vacuo (6–7 mbar) at 100° for 10 hours. 3.83 g (=92.7% yield) of 4-amino-2-(4,4-dimethyl-2-oxo-1-imidazolidinyl)pyrimidine-5-carboxylic acid N-ethyl-N-(3-trifluoromethylphenyl)amide hydrochloride were obtained, melting point 264°–265° (decomposition).

$C_{19}H_{22}ClF_3N_6O_2$ (458.89) Calculated: C 49.73 H 4.83 Cl 7.73 F 12.42 N 18.32% Found: C 48.9 H 5.0 Cl 7.6 F 12.3 N 17.8%

EXAMPLE 3

A suspension of 1.746 g (4 mmol) of a compound II in which $R^1$ and $R^2$ are $CH_3$, $R^3$, $R^5$ and $R^6$ are hydrogen and $R^4$ is isopropyl in 4 ml of glacial acetic acid was stirred at 50° for 3 hours and subsequently evaporated in vacuo. The remaining residue was dissolved in 5 ml of 2N hydrochloric acid and 10 ml of ether. After separation of the phases, the aqueous hydrochloric acid phase was extracted several times with ether, subsequently adjusted to pH 9–10 with 6N sodium hydroxide solution and then extracted several times with $CH_2Cl_2$. The combined $CH_2Cl_2$ extracts were washed with a few ml of water and dried with $Na_2SO_4$. After filtration, the $CH_2Cl_2$ was stripped off in vacuo, and the remaining residue was dissolved in 5–6 ml of ether. Crystallization took place from the ether solution. The crystalline substance was filtered off with suction, washed with ether and dried at 100° for 16 hours. 1.14 g (=65.3% yield) of TLC-pure 4-amino-2-(4,4-dimethyl-2-oxo-1-imidazolidinyl)pyrimidine-5-carboxylic acid N-isopropyl-N-(3-trifluoromethylphenyl)amide were obtained, melting 202°–203°.

$C_{20}H_{23}F_3N_6O_2$ (436.45) Calculated: C 55.04 H 5.31 F 13.06 N 19.26% Found: C 55.0 H 5.5 F 12.4 N 19.1%

EXAMPLE 4

2.5 ml of a 6.6 molar solution of HCl in ether were added dropwise to a solution of 6.55 g (15 mmol) of 4-amino-2-(4,4-dimethyl-2-oxo-1-imidazolidinyl)pyrimidine-5-carboxylic acid N-isopropyl-N-(3-trifluoromethylphenyl)amide prepared as in Example 3 in 35 ml of acetone at room temperature, and the resulting suspension was stirred at room temperature for 2 hours. The crystals were then filtered off with suction, washed with acetone and dried in vacuo at 100° for 10 hours. 6.84 g (=96.5% yield) of 4-amino-2-(4, 4-dimethyl-2-oxo-1-imidazolidinyl)pyrimidine-5-carboxylic acid N-isopropyl-N-(3-trifluoromethylphenyl)amide hydrochloride were obtained, melting point 279°–280° (decomposition).

$C_{20}H_{24}ClF_3N_6O_2$ (472.92) Calculated: Cl 7.50% Found: Cl•7.6%

EXAMPLE 5

A suspension of 16.70 g (37 mmol) of a compound II in which $R^1$ and $R^2$ are $CH_3$, $R^3$, $R^5$ and $R^6$ are hydrogen and $R^4$ is n-butyl in 41 ml of glacial acetic acid was stirred at 60° for 4 hours, resulting in a solution. This was evaporated in vacuo. The residue was taken up in 300 ml of $CH_2Cl_2$, and this solution was extracted three times with 40 ml of 2N NaOH each time and twice with 50 ml of water each time. The $CH_2Cl_2$ solution was dried and filtered and then evaporated in vacuo. The remaining oily residue (16.5 g) was dissolved in 15 ml of ethyl acetate, and ether was added to incipient opalescence, after which crystals separated out. The solid was stirred in an ice bath for 2 hours and then filtered off with suction, washed with ether and dried at 100° for 20 hours. 9.48 g (56.8% yield) of pure 4-amino-2-(4,4-dimethyl-2-oxo-1-imidazolidinyl)pyrimidine-5-carboxylic acid N-butyl-N-(3trifluoromethylphenyl)amide were obtained, melting point 154°–155°.

$C_{21}H_{25}F_3N_6O_2$ (450.48) Calculated: C 55.99 H 5.59 F 12.65 N 18.66% Found: C 55.3 H 5.6 F 12.5 N 18.4%

EXAMPLE 6

1.9 ml of a 6.17 molar solution of HCl in ether were added to a solution of 4.96 g (11 mmol) of the compound I ($R^1$, $R^2$=$CH_3$; $R^3$, $R^5$, $R^6$=H; $R^4$=n-$C_4H_9$) prepared as in the previous example in 25 ml of acetone at room temperature. The resulting suspension was stirred while cooling in ice for 2 hours. The crystals were then filtered off with suction, washed with acetone and ether and dried in vacuo (6 mbar) at 100° for 15 hours. 5.44 g (~100%) of pure 4-amino-2-(4,4-dimethyl-2-oxo-1-imidazolidinyl)pyrimidine-5-carboxylic acid N-butyl-N-(3-trifluromethylphenyl)amide hydrochloride were obtained, melting point 266°–267° (decomposition).

$C_{21}H_{26}ClF_3N_6O_2$ (486.94) Calculated: Cl•7.28% Found: Cl•7.3%

EXAMPLE 7

In accordance with the procedure described in Example 5, 14.76 g (32.8 mmol) of a compound II ($R^1$, $R^2$=$CH_3$; $R^3$, $R^5$, $R^6$=H; $R^4$=sec.-$C_4H_9$) and 36 ml of glacial acetic acid were stirred at 60° for 4 hours. Working up was then carried out as described in Example 5. 9.17 g (62% yield) of TLC-pure 4-amino-2-(4,4-dimethyl-2-oxo-1-imidazoidinyl)pyrimidine-5-carboxYlic acid N-sec.-butyl-N-(3-trifluoromethylphenyl)amide were obtained, melting point 149°–150°.

$CH_{21}H_{25}F_3N_6O_2$ (450.48) Calculated: C 55.59 H 5.59 F 12.65 N 18.66% Found: C 55.8 H 5.5 F 12.3 N 18.6%

EXAMPLE 8

In accordance with the procedure described in Example 6, 4.51 g (10 mmol) of the compound I ($R^1$, $R^2$=$CH_3$; $R^3$, $R^5$, $R^6$=H; $R^4$=sec.-$C_4H_9$) prepared as in Example 7 were converted into the hydrochloride. 4.81 g (=98.8%) of pure 4-amino-2-(4,4-dimethyl-2-oxo-1-imidazolidinyl)-pyrimidine-5-carboxylic acid N-sec.-butyl-N-(3-trifluoromethylphenyl)amide hydrochloride were obtained, melting point 282°–283° (decomposition).

$C_{21}H_{26}ClF_3N_6O_2$ (486.94) Calculated: Cl•7.28% Found: Cl•7.35%

EXAMPLE 9

A mixture of 13.57 g (26.9 mmol) of a compound II ($R^1$, $R^2$=$CH_3$; $R^3$, $R^5$.$R^6$=H; $R^4$=CH($CH_3$)—$CH_2CH_2$—CH=C($CH_3$)$_2$) and 30 ml of glacial acetic acid was stirred at 50°–55° for 4 hours, a solution being present after 15 minutes. The mixture was then evaporated in vacuo. The remaining residue (11.3 g) was chromatographed on a silica gel/$CH_2Cl_2$ column (28 mm ø×400 mm (H)). After elution with 900 ml $CH_2Cl_2$, 1.5 g of preliminary zones were isolated. Elution was then carried out with $CH_2Cl_2$/$C_2H_5OH$ 100:1 to 10:1 (with continuously increasing $C_2H_5OH$ content) in 7 fractions (400 ml each) to give 8.7 g of almost pure to pure required product in oily form. From this were obtained by crystallization from isopropyl ether/isohexane 7.1 g of pure 4-amino-2-(4,4-dimethyl-2-oxo-1-imidazolidinyl)pyrimidine-5-carboxylic acid N-(2-methyl-2-hepten-6-yl)-N-(3-trifluoromethylphenyl)amide, melting point 106°–107°. The mother liquor residue (1.06 g) was likewise almost pure compound I ($R^1$, $R^2$=$CH_3$; $R^3$, $R^5$, $R^6$=H; $R^4$=CH($CH_3$)—$CH_2CH_2$—CH=C($CH_3$)$_2$) so that in total 8.16 g (=60% yield) of this compound had been obtained.

$C_{25}H_{31}F_3N_6O_2$ (504.57) Calculated: C 59.51 H 6.19 F 11.30 N 16.66% Found: C 59.5 H 6.2 F 11.0 N 16.4%

EXAMPLE 10

3.50 g (=94% yield) of pure crystalline 4-amino-2-(4,4-dimethyl-2-oxo-1-imidazolidinyl)pyrimidine-5-carboxylic acid N-(2-methyl-2-hepten-6-yl)-N-(3-trifluoromethylphenyl)amide hydrochloride, melting point 248°–249°, were obtained as in Example 6 starting from 3.46 g (6.86 mmol) of the compound I ($R^1$, $R^2$=$CH_3$; $R^3$, $R^5$, $R^6$=H; $R^4$=CH($CH_3$)—$CH_2CH_2$—CH=C($CH_3$)$_2$, which had been obtained as in previous Example 9 and was dissolved in 20 ml of ethyl acetate, and 1.06 ml of a 6.6 molar solution of HCl in ether.

$C_{25}H_{32}ClF_3N_6O_2$ (541.04) Calculated: Cl•6.55% Found: Cl•6.5%

EXAMPLE 11

In accordance with the procedure described in Example 5, 10.0 g (22.3 mmol) of a compound II ($R^1$, $R^2$=$CH_3$; $R^3$, $R^5$, $R^6$=H; $R^4$=cyclopropylmethyl) and 24.6 ml of glacial acetic acid were stirred at 60° for 4 hours (a solution was present after stirring for 20 minutes) and subsequently worked up as in Example 5. 6.67 g (66.7% yield) of TLC-pure 4-amino-2-(4,4-dimethyl-2-oxo-1-imidazolidinyl)pyrimidine-5-carboxylic acid N-cyclopropylmethyl-N-(3-trifluoromethylphenyl)amide were obtained, melting point 193°–194°.

$C_{21}H_{23}F_3N_6O_2$ (448.46) Calculated: C 56.24 H 5.17 F 12.71 N 18.74% Found: C 55.9 H 5.1 F 12.1 N 18.9%

EXAMPLE 12

In accordance with the procedure described in Example 6, 5.67 g (12.64 mmol) of the compound I ($R^1$, $R^2$=$CH_3$; $R^3$, $R^5$, $R^6$=H; $R^4$=cyclopropylmethyl) prepared as in Example 11 were converted into the hydrochloride. 5.84 g (=95.3%) of pure 4-amino-2-(4,4-dimethyl-2-oxo-1-imidazolidinyl)pyrimidine-5-carboxylic acid N-cyclopropylmethyl-N-(3-trifluoromethylphenyl)amide hydrochloride were obtained, melting point 265°–266°.

$C_{21}H_{24}ClF_3N_6O_2$ (484.93) Calculated: Cl•7.31% Found: Cl•7.5%

In accordance with the procedure described in Example 5, the compounds I ($R^1$, $R^2$=$CH_3$; $R^3$=H, cf. formula hereinafter) listed in Examples 13–27 in the following Table 3 were prepared.

The hydrochlorides (Examples 28–42) were prepared by the procedure described in Example 6 from the compounds (Examples 13–27) listed in Table 3, and are compiled in Table 4 hereinafter.

TABLE 3

Examples 13-27

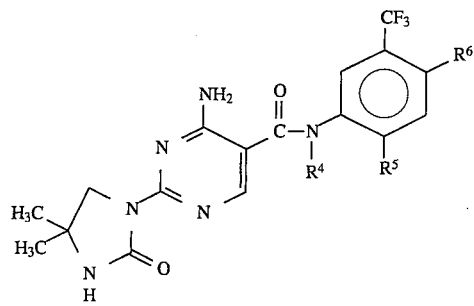

| Ex. No. | $R^4$ | $R^5$ | $R^6$ | m.p. [°C.] | Calc. C | H | F | N | Found C | H | F | N | Yield [%] |
|---|---|---|---|---|---|---|---|---|---|---|---|---|---|
| 13 | $CH_3$ | F | H | 168–69 | 50.70 | 4.26 | 17.82 | 19.71 | 50.1 | 4.4 | 17.1 | 19.4 | 53.2 |
| 14 | $CH_3$ | Cl | H | 269–70 | 48.82 | 4.10 | 12.97 | 18.98 | | | | | 45.0 |
| 15 | $CH_3$ | H | Br | 233 | 44.37 | 3.72 | 11.70 | 17.25 | | | | | 37.6 |
| 16 | $C_2H_5$ | Cl | H | 145 | 49.95 | 4.41 | 12.48 | 18.40 | | | | | 44.8 |
| 17 | $C_2H_5$ | F | H | 200–01 | 51.82 | 4.58 | 17.26 | 19.08 | 51.8 | 4.5 | 16.2 | 19.2 | 55.4 |
| 18 | $n\text{-}C_3H_7$ | H | H | 114 | 55.04 | 5.31 | 13.06 | 19.26 | | | | | 31.0 |
| 19 | $n\text{-}C_3H_7$ | Cl | H | 238 | 51.02 | 4.71 | 12.10 | 17.85 | | | | | 46.7 |
| 20 | $i\text{-}C_3H_7$ | H | F | 218–19 | 52.96 | 4.88 | 16.72 | 18.49 | 52.9 | 4.5 | 16.6 | 18.1 | 77.3 |
| 21 | $CH_2CH(CH_3)_2$ | H | H | 126 | 55.99 | 5.59 | 12.65 | 18.66 | | | | | 4.62 |
| 22 | $CH_2C(CH_3)_3$ | H | H | 219–20 | 56.89 | 5.86 | 12.27 | 18.09 | 56.9 | 5.8 | 11.8 | 18.1 | 62.4 |
| 23 | $CH(CH_3)CH_2CH(CH_3)_2$ | H | H | 199–200 | 57.73 | 6.11 | 11.91 | 17.56 | 57.9 | 6.3 | 11.8 | 17.6 | 66.2 |
| 24 | $CH(CH_3)CH_2CH(CH_3)_2$ | H | F | 195–96 | 55.64 | 5.68 | 15.31 | 16.93 | 54.2 | 5.5 | 15.2 | 16.5 | 73.2 |
| 25 | $CH_2CH=CH_2$ | H | H | 189–90 | 55.29 | 4.87 | 13.12 | 19.35 | 55.2 | 5.1 | 12.6 | 19.3 | 68.3 |
| 26 | $CH_3$–cyclopropyl | F | H | 209–10 | 54.07 | 4.75 | 16.29 | 18.02 | 54.2 | 4.7 | 16.0 | 18.1 | 66.4 |
| 27 | cyclopentyl | H | H | 135–40 | 57.13 | 5.45 | 12.32 | 18.17 | 57.3 | 5.3 | 11.9 | 18.3 | 66.8 |

TABLE 4

Examples 28–42
Hydrochlorides of the compounds I listed in Examples 13–27 in Table 3

| Ex. No. | Hydrochloride of the compound of Example | m.p. [°C.] | Cl Calc. | Cl Found |
|---|---|---|---|---|
| 28 | 13 | 269–70 | 7.66 | 7.4 |
| 29 | 14 | 271–73 | 14.79 | 14.3 |
| 30 | 15 | 250 | 6.78 | 6.6 |
| 31 | 16 | 288 | 14.37 | 14.0 |
| 32 | 17 | 278–79 | 7.44 | 7.4 |
| 33 | 18 | 251 | 7.50 | 7.3 |
| 34 | 19 | 293 | 13.98 | 13.7 |
| 35 | 20 | 284–85 | 7.22 | 7.2 |
| 36 | 21 | 264 | 7.28 | 7.1 |
| 37 | 22 | 285–86 | 7.08 | 6.8 |
| 38 | 23 | 274–75 | 6.88 | 6.8 |
| 39 | 24 | 281–82 | 6.65 | 6.7 |
| 40 | 25 | 268–69 | 7.53 | 7.5 |
| 41 | 26 | 282–83 | 7.05 | 6.6 |
| 42 | 27 | 270–72 | 7.11 | 7.2 |

EXAMPLE 43

A mixture of 2.86 g (7 mmol) of a compound II ($R^1=CH_3$; $R^2$, $R^3$, $R^5$, $R^6$=H; $R^4=C_2H_5$), 5 ml of glacial acetic acid and 0.70 ml of a 6.17 molar solution of HCl in ether was stirred at 70° for 2 hours (a solution was produced after 7 minutes) and then evaporated in vacuo. The residue was taken up in 80 ml of $CH_2Cl_2$, the solution was extracted three times with 15 ml of N NaOH each time and twice with 7 ml of water each time, the $CH_2Cl_2$ solution was dried over $Na_2SO_4$ and, after filtration, this solution was evaporated in vacuo. The remaining residue was partially dissolved in 2 ml of ethyl acetate. Crystallization took place after addition of ether. After stirring in an ice bath for 1 hour, the crystals were filtered off with suction, washed with ether and dried in vacuo (5–8 mbar) at 100° for 15 hours. 1.88 g (=65.7% yield) of TLC-pure 4-amino-2-(4-methyl-2-oxo-1-imidazolidinyl)pyrimidine-5-carboxylic acid N-ethyl-N-(3-trifluoromethylphenyl)amide were obtained, melting point 207°–208° (cf. Examples 56 and 57 in this connection).

EXAMPLE 44

A mixture of 2.53 g (6 mmol) of a compound II ($R^1$, $R^2=CH_3$; $R^3$, $R^5$, $R^6$=H; $R^4=C_2H_5$), 360 mg (4 mmol) oxalic acid and 5 ml of propionic acid was stirred at 70° for 2 hours (a solution was present after 10 minutes) and then evaporated in vacuo. The remaining residue was worked up further as described in Example 43. 1.72 g (=68% yield) of pure 4-amino-2-(4,4-dimethyl-2-oxo-1-imidazolidinyl)pyrimidine-5-carboxylic acid N-ethyl-N-(3-trifluoromethylphenyl)amide were obtained, melting point 186°–187° (cf. Example 1 in this connection).

EXAMPLE 45

A mixture of 4.645 g (10 mmol) of a compound II ($R^1$, $R^2=CH_3$; $R^3$, $R^5$, $R^6$=H; $R^4$=n-$C_5H_{11}$), 300 mg of anhydrous oxalic acid and 8.33 ml of anhydrous formic acid was stirred at 50° for 3 hours, a solution being produced after 10 minutes. The mixture was then evaporated in vacuo, and the residue was dissolved in 100 ml of ethyl acetate. 20 ml of 2N NaOH were added to this solution, which was shaken for 5 minutes. After phase separation, the organic solution was extracted three times with 2 ml of 2N NaOH each time and twice with 10 ml of water each time, dried over MgSO$_4$, filtered and evaporated in vacuo. The residue was taken up in ether, whereupon crystallization took place. The crystalline substance was isolated by filtration with suction and dried in vacuo at 100° for 17 hours. 2.88 g (=62% yield) of pure 4-amino-2-(4,4-dimethyl-2-oxo-1-imidazolidinyl)pyrimidine-5-carboxylic acid N-pentyl-N-(3-trifluoromethylphenyl)amide were obtained, melting point 167°–168° C.

$C_{22}H_{27}F_3N_6O_2$ (464.51) Calculated: C 56.89 H 5.86 F 12.27 N 18.09% Found: C 56.7 H 6.1 F 12.0 N 18.1%

EXAMPLE 46

A mixture of 4.645 g (10 mmol) of a compound II ($R^1$, $R^2$=CH$_3$; $R^3$, $R^5$, $R^6$=H; $R^4$=n-C$_5$H$_{11}$), 300 mg of anhydrous oxalic acid and 9 ml of glacial acetic acid was stirred at 60° for 3 hours and then worked up in the same way as described in the preceding Example 45. 3.13 g (=67.5% yield) of the same compound as described in Example 45 were obtained, melting point 167°–168°.

EXAMPLE 47

In accordance with the procedure described in Example 6, 5.11 g (11 mmol) of the compound I ($R^1$, $R^2$=CH$_3$; $R^3R^5$, $R^6$=H; $R^4$=n-C$_5$H$_{11}$) prepared as in Examples 45 and 46 were converted into the hydrochloride. 5.35 g (=97.1% yield) of pure 4-amino-2-(4,4-dimethyl-2-oxo-1-imidazolidinyl)pyrimidine-5-carboxylic acid N-pentyl-N-(3-trifluoromethylphenyl)amide hydrochloride were obtained, melting point 246°–247°.

$C_{22}H_{28}ClF_3N_6O_2$ (500.97) Calculated: C 52.75 H 5.63 Cl•7.08 F 11.38 N 16.78% Found: C 52.8 H 5.4 Cl•6.6 F 10.9 N 16.8%

EXAMPLE 48

A mixture of 3.944 g (10 mmol) of a compound II ($R^1$=CH$_3$; $R^2$, $R^3$, $R^5$, $R^6$=H; $R^4$=CH$_3$), 300 mg of anhydrous oxalic acid and 8.7 ml of glacial acetic acid was stirred at 60° for 3 hours, a solution being produced after about 30 minutes. The latter was evaporated in vacuo, and the residue was taken up in 100 ml of CH$_2$Cl$_2$. The resulting mixture was vigorously mixed with 20 ml of 2N NaOH. After separation of the phases, the organic phase was extracted successively twice with 6 ml of N NaOH each time and twice with 10 ml of water each time, dried over MgSO$_4$, filtered and evaporated in vacuo. The remaining residue was taken up in 15 ml of ether, whereupon crystallization started immediately. The crystalline substance was isolated by filtration with suction and was dried in vacuo (6 mbar) at 100° for 15 hours. 2.80 g (=71% yield) of pure 4-amino-2-(4-methyl-2-oxo-1-imidazolidinyl)pyrimidine-5-carboxylic acid N-methyl-N-(3-trifluoromethylphenyl)amide were obtained, melting point 237°–38°.

$C_{17}H_{17}F_3N_6O_2$ (394.37) Calculated: C 51.78 H 4.35 F 14.45 N 21.31% Found: C 51.5 H 4.4 F 14.5 N 21.0%

EXAMPLE 49

In the same batch size and by the same procedure as described in Example 48, the same compound II was cyclized in the presence of 360 mg of oxalic acid (instead of 300 mg as in Example 48). This resulted in 2.77 g (=70.2% yield) of the compound I ($R^1$=CH$_3$; $R^2$, $R^3$, $R^5$, $R^6$=H; $R^4$=CH$_3$) as in Example 48, melting point 237°–238°.

EXAMPLE 50

As in Example 6, 4.34 g (11 mmol) of the compound I ($R^1$=CH$_3$; $R^2$, $R^3$, $R^5$, $R^6$=H; $R^4$=CH$_3$) prepared as in Examples 48 and 49 were converted into the hydrochloride. 4.71 g (=99.4% yield) of pure 4-amino-2-(4-methyl-2-oxo-1-imidazolidinyl)pyrimidine-5-carboxylic acid N-methyl-N-(3-trifluoromethylphenyl)amide hydrochloride were obtained, melting point 190°–192°.

$C_{17}H_{18}ClF_3N_6O_2$ (430.84) Calculated: Cl•8.23% Found: Cl•8.1%

EXAMPLE 51

In accordance with the procedure described in Example 5, 0.54 g (1.2 mmol) of a compound II ($R^1$=CH$_3$; $R^2$, $R^3$, $R^5$, $R^6$=H; $R^4$=cyclopentyl) and 1.32 ml of glacial acetic acid were stirred at 60° for 4 hours and subsequently worked up. 0.32 g (59.3% yield) of TLC-pure 4-amino-2-(4-methyl-2-oxo-1-imidazolidinyl)pyrimidine-5-carboxylic acid N-cyclopentyl-N-(3-trifluoromethylphenyl)amide was obtained, melting point 219°–220° (from ethyl acetate<< ether).

$C_{21}H_{23}F_3N_6O_2$ (448.46) Calculated: C 56.24 H 5.17 F 12.71 N 18.74% Found: C 56.0 H 5.1 F 12.6 N 18.5%

EXAMPLE 52

As in Example 6, 126 mg (0.28 mmol) of the compound I ($R^1$=CH$_3$; $R^2$, $R^3$, $R^5$, $R^6$=H; $R^4$=cyclopentyl) prepared as in Example 51 were converted into the hydrochloride. 135 mg (=99.4%) of pure 4-amino-2-(4-methyl-2-oxo-1-imidazolidinyl)pyrimidine-5-carboxylic acid N-cyclopentyl-N-(3-trifluoromethylphenyl)amide hydrochloride were obtained, melting point 270°–271°.

$C_{21}H_{24}ClF_3N_6O_2$ (484.93) Calculated: Cl•7.31% Found: Cl•7.2%

EXAMPLE 53

As in Example 51, 1.80 g (4.26 mmol) of 1-cyano-1-[N-butyl-N-(3-trifluoromethylphenyl)carbamoyl]-2-[imino(2-oxo-1-imidazolidinyl)methylamino]ethene (compound II, $R^1$, $R^2$, $R^3$, $R^5$, $R^6$=H; $R^4$=n-C$_4$H$_9$) and 4.7 ml of glacial acetic acid were stirred at 60° for 4 hours and subsequently worked up. 0.85 g (=47.3% yield) of pure 4-amino-2-(2-oxo-1-imidazolidinyl)pyrimidine-5-carboxylic acid N-butyl-N-(3-trifluoromethylphenyl)amide was obtained, melting point 234°–235°.

$C_{19}H_{21}F_3N_6O_2$ (422.43) Calculated: C 54.02 H 5.01 F 13.49 N 19.90% Found: C 54.1 H 4.9 F 12.8 N 20.0%

EXAMPLE 54

A mixture of 1.32 g (3.12 mmol) of a compound II ($R^1$, $R^2$, $R^3$, $R^5$, $R^6$=H; $R^4$=n-C$_4$H$_9$), 94 mg (1.04 mmol) of anhydrous oxalic acid and 2.81 ml of glacial acetic acid was stirred at 60° for 3 hours and then worked up as described in Example 5. The resulting residue (1.08 g) was crystallized from ether. 0.91 g (=69% yield) of pure compound I in which $R^1$, $R^2$, $R^3$, $R^5$ and $R^6$ are H and $R^4$ is n-C$_4$H$_9$ was obtained (cf. Example 53), melting point 234°–235°.

EXAMPLE 55

As in Example 6, 1.65 g (3.9 mmol) of the compound I obtained as in Examples 53 and 54 were converted into the hydrochloride. This resulted in 1.74 g (97.2%) of 4-amino-2-(2-oxo-1-imidazolidinyl)pyrimidine-5-carboxylic acid N-butyl-N-(3-trifluoromethylphenyl)amide hydrochloride, melting point 212°–213°.

$C_{19}H_{22}ClF_3N_6O_2$ (458.89) Calculated: Cl•7.73% Found: Cl•7.7%

EXAMPLE 56

A mixture of 4.084 g (10 mmol) of a compound II ($R^1$=$CH_3$; $R^2$, $R^3$, $R^5$, $R^6$=H; $R^4$=$C_2H_5$), 360 mg (4 mmol) of anhydrous oxalic acid and 9 ml of glacial acetic acid was stirred at 60° for 3 hours and then worked up as described in Example 5. 2.83 g (69.3% yield) of pure 4-amino-2-(4-methyl-2-oxo-1-imidazolidinyl)pyrimidine-5-carboxylic acid N-ethyl-N-(3-trifluoromethylphenyl)amide were obtained (by crystallization from ether) after drying, melting point 208°–209°.

$C_{18}H_{19}F_3N_6O_2$ (408.40) Calculated: C 52.94 H 4.69 F 13.96 N 20.58% Found: C 52.5 H 4.5 F 12.4 N 20.8%

EXAMPLE 57

In the same batch size (10 mmol), the same compound II as in Example 56 was stirred with 540 mg of anhydrous oxalic acid (6 mmol) and 8.5 ml of glacial acetic acid at 60° for 3 hours. Working up in analogy to the description in Example 5 resulted in 2.86 g (70% yield) of compound I ($R^1$=$CH_3$; $R^2$, $R^3$, $R^5$, $R^6$=H; $R^4$=$C_2H_5$), melting point 208°–209°.

EXAMPLE 58

As in Example 6, 4.57 g (93.4% yield) of 4-amino-2-(4-methyl-2-oxo-1-imidazolidinyl)pyrimidine- 5-carboxylic acid N-ethyl-N-(3-trifluoromethylphenyl)amide hydrochloride, melting point 242°–243°, were obtained starting from 4.49 g (11 mmol) of the compound I prepared as in Examples 56 and 57.

$C_{18}H_{20}ClF_3N_6O_2$ (444.86) Calculated: Cl•7.97% Found: Cl•8.2[{]jf44b

EXAMPLE 59 a) A mixture of 6.34 g (15 mmol) of a compound II ($R^1$, $R^2$=$CH_3$; $R^3$, $R^5$, $R^6$=H; $R^4$=$C_2H_5$), 450 mg of anhydrous oxalic acid and 13 ml of glacial acetic acid was stirred at 65° for 3 hours and subsequently worked up as described in Example 5. Crystallization from ether resulted in 4.52 g (=71.3% yield) of a compound I ($R^1$, $R^2$=$CH_3$; $R^3$, $R^5$, $R^6$=H; $R^4$=$C_2H_5$), melting point 186°–187°.

b) In an analogous manner, a mixture of 5.07 g (12 mmol) of the same compound II, 360 mg of anhydrous oxalic acid and 10.4 ml of anhydrous formic acid was stirred at 65° for 3 hours and subsequently worked up. 3.04 g (=60% yield) of the compound I ($R^1$, $R^2$=$CH_3$; $R^3$, $R^5$, $R^6$=H; $R^4$=$C_2H_5$) were obtained, melting point 186°–87°.

EXAMPLE 60

2.05 ml of a molar solution of $HNO_3$ in ethyl acetate were added to a suspension of 881 mg (2 mmol) of 4-amino-2-(4,4-dimethyl-2-oxo-1-imidazolidinyl)pyrimidine-5-carboxylic acid N-ethyl-N-(2-fluoro-5-trifluoromethylphenyl)amide (compound I from Example 17) in 13.3 ml of ethyl acetate at room temperature. This briefly resulted in a solution, from which a crystalline substance separated out. The latter was, after stirring (in an ice bath) for 1 hour, filtered off with suction, washed with ethyl acetate and ether and dried at 80° in vacuo (6–8 mbar) for 15 hours. 1.02 g of 4-amino-2-(4,4-dimethyl-2-oxo-1-imidazolidinyl)pyrimidine-5-carboxylic acid N-ethyl-N-(2-fluoro-5-trifluoromethylphenyl)amide nitrate were obtained, melting point 235°–236°. This nitrate is soluble in a concentration of 1.7% by weight in water, i.e. 1 part dissolves in 57.5 parts of water.

$C_{19}H_{21}F_4N_7O_5$ (503.43) Calculated: C 45.33 H 4.20 F 15.10 N 19.48% Found: C 44.8 H 4.5 F 14.6 N 19.1%

EXAMPLE 61

0.38 ml of a 33% strength solution of HBr in glacial acetic acid was added to a solution of 933 mg (2 mmol) of 4-amino-2-(4,4-dimethyl-2-oxo-1-imidazolidinyl)pyrimidine-5-carboxylic acid N-cyclopropylmethyl-N-(2-fluoro-5-trifluoromethylphenyl)amide (compound I from Example 26) in 6 ml of acetone at room temperature. A crystalline substance then separated out. After stirring in an ice bath for 2 hours, the solid was filtered off with suction, washed with ether and dried in vacuo (6–7 mbar) for 16 hours. 1.06 g of hydrobromide of the compound I employed (from Example 26) (=96.8% yield) were obtained, melting point 296°. This hydrobromide is soluble in a concentration of 1.5% by weight in water, i.e. 1 part dissolves in 65.8 parts of water.

$C_{21}H_{23}BrF_4N_6O_2$ (547.37) Calculated: C 46.08 H 4.24 Br 14.60 N 15.35% Found: C 45.9 H 3.9 Br 14.7 N 15.5%

EXAMPLE 62

A mixture of 2.66 g (7 mmol) of a compound II ($R^1$, $R^2$, $R^3$, $R^5$, $R^6$=H; $R^4$=$CH_3$), 0.72 g (8 mmol) of anhydrous oxalic acid and 4.5 ml of glacial acetic acid was stirred at 85° for 1 hour and subsequently worked up as in Example 5. 1.58 g (=59.4% yield) of TLC-pure 4-amino-2-(2-oxo-1-imidazolidinyl)pyrimidine-5-carboxylic acid N-methyl-N-(3-trifluoromethylphenyl)amide were obtained, melting point 249°–250°.

$C_{16}H_{15}F_3N_6O_2$ (380.35) Calculated: C 50.53 H 3.98 F 14.99 N 22.10% Found: C 50.3 H 3.9 F 14.7 N 22.0%

EXAMPLE 63

A mixture of 2.17 g (5.7 mmol) of the same compound II as in Example 62, 600 mg of polyphosphoric acid (from Riedel-de-Haen) and 5.7 ml of glacial acetic acid was stirred at 70° for 2 hours and subsequently worked up as in Example 5. After this, 0.89 g (=41% yield) of the compound I ($R^1$, $R^2$, $R^3$, $R^5$, $R^6$=H; $R^4$=$CH_3$) prepared in Example 62 was obtained, melting point 249°–50°.

EXAMPLE 64

2.853 g (7.5 mmol) of the compound I prepared as in Examples 62 and 63 were converted into the hydrochloride as in Example 6. 3.12 g of 4-amino-2-(2-oxo-1-imidazolidinyl)pyrimidine-5-carboxylic acid N-methyl-N-(3-trifluoromethylphenyl)amide hydrochloride were obtained, melting point 201°–202°.

$C_{16}H_{16}ClF_3N_6O_2$ (416.81) Calculated: Cl•8.51% Found: Cl•8.1%

EXAMPLE 65

A mixture of 2.535 g (6 mmol) of a compound II ($R^1$, $R^2$=$CH_3$; $R^3$, $R^5$, $R^6$=H; $R^4$=$C_2H_5$), 841 mg (4 mmol) of citric acid monohydrate and 4.25 ml of glacial acetic acid was stirred at 70° for 2 hours and subsequently worked up as in Example 5.1.86 g (=73.4% yield) of pure compound I ($R^1$, $R^2$=$CH_3$; $R^3$, $R^5$, $R^6$=H; $R^4$=$C_2H_5$) were obtained, melting point 186°–187°.

EXAMPLE 66

A mixture of 2.775 g (6 mmol) of a compound II ($R^1$, $R^2$=$CH_3$; $R^3$, $R^5$, $R^6$=H; $R^4$=cyclopentyl), 645 mg (5 mmol) of dichloroacetic acid and 4.25 ml of glacial acetic acid was subjected to the process described in Example 65. 1.45 g (=52.3% yield) of 4-amino-2-(4,4-dimethyl-2-oxo-1-imidazolidinyl)pyrimidine-5-carboxylic acid N-cyclopentyl-N-(3-trifluoromethylphenyl)amide were obtained, melting point 135°–39°.

EXAMPLE 67

A mixture of 2.535 g (6 mmol) of a compound II ($R^1$, $R^2$=$CH_3$; $R^3$, $R^5$, $R^6$=H; R4=$C_2H_5$), 820 mg (5 mmol) of trichloroacetic acid and 4.25 ml of glacial acetic acid was subjected to the process described in Example 65. 1.97 g (77.7% yield) of TLC-pure 4-amino-2-(4,4-dimethyl-2-oxo-1-imidazolidinyl)pyrimidine-5-carboxylic acid N-ethyl-N-(3-trifluoromethylphenyl)amide were obtained.

EXAMPLE 68

A mixture of 3.04 g (7 mmol) of a compound II ($R^1$, $R^2$=$CH_3$; $R^3$, $R^5$, $R^6$=H; $R_4$=$CH_2CH$=$CH_2$), 665 mg (5.83 mmol) of trifluoroacetic acid and 5 ml of glacial acetic acid was subjected to the process described in Example 65. 2.00 g (65.8% yield) of 4-amino-2-(4,4-dimethyl-2-oxo-1-imidazolidinyl)pyrimidine-5-carboxylic acid N-allyl-N-(3-trifluoromethylphenyl)amide were obtained, melting point 187°–88°.

EXAMPLE 69

A mixture of 3.04 g (7 mmol) of the same compound II as in Example 68, 515 mg (4.44 mmol) of fumaric acid and 6 ml of glacial acetic acid was stirred at 85° for 1 hour and subsequently worked up as in Example 5. 2.08 g (=68.4% yield) of the same compound I as in Example 68 were obtained, melting point 188°–89°.

EXAMPLE 70

A mixture of 2.84 g (7 mmol) of a compound II ($R^1$=CH=$CH_2$; $R^2$, $R^3$, $R^5$, $R^6$=H; $R^4$=$CH_3$), 486 mg (5.5 mmol) of cyanoacetic acid and 5 ml of glacial acetic acid was stirred at 75° for 1.5 hours and subsequently worked up as in Example 5. Crystallization from ether resulted in 1.75 g (=61.6% yield) of 4-amino-2-(4-vinyl-2-oxo-1-imidazolidinyl)pyrimidine-5-carboxylic acid N-methyl-N-(3-trifluoromethylphenyl)amide, melting point 203°–204°.

$C_{18}H_{17}F_3N_6O_2$ (406.38) Calculated: C 53.20 H 4.22 F 14.03 N 20.68% Found: C 53.3 H 4.3 F 14.0 N 20.4%

EXAMPLE 71

A mixture of 2.84 g (7 mmol) of the same compound II as in Example 70, 5 ml of glacial acetic acid and 0.90 ml of a 6.17 molar solution of HCl in ether was stirred at 70° for 2 hours and subsequently as in Example 5. 2.0 g (70.4% yield) of the same compound I as in Example 70 were obtained, melting point 203°–204°.

EXAMPLE 72

4.07 g (10 mmol) of the compound I prepared as in Examples 70 and 71 were converted into the hydrochloride as in Example 6. 4.10 g (92.6% yield) of 4-amino-2-(4-vinyl-2-oxo-1-imidazolidinyl)pyrimidine-5-carboxylic acid N-methyl-N-(3-trifluoromethylphenyl)amide hydrochloride were obtained, melting point 210°–211°.

$C_{18}H_{18}ClF_3N_6O_2$ (442.85) Calculated: Cl•8.01% Found: Cl•7.7%

EXAMPLE 73

A mixture of 2.84 g (7 mmol) of the same compound II as in Example 70, 1.05 g of p-toluenesulfonic acid monohydrate and 5 ml of glacial acetic acid was stirred at 70° for 2 hours and then worked up as. in Example 5. 2.03 g (=71.5% yield) of pure 4-amino-2-(4-vinyl-2-oxo-1-imidazolidinyl)pyrimidine-5-carboxylic acid N-methyl-N-(3-trifluoromethylphenyl)amide were obtained, melting point 203°–204°.

EXAMPLE 74

A mixture of 3.06 g (7 mmol) of a compound II ($R^1$=$CH_3$; $R^2$, $R^3$, $R^5$, $R^6$=H; $R^4$=$CH_2CH(CH_3)_2$, 1.0 ml of a 33% strength solution of HBr in glacial acetic acid (~5.6 mmol) and 5 ml of glacial acetic acid was stirred at 75° for 1.5 hours and then worked up as in Example 5. 1.37 g (44.8% yield) of 4-amino-2-(4-methyl-2-oxo-1-imidazolidinyl)pyrimidine-5-carboxylic acid N-isobutyl-N-(3-trifluoromethylphenyl)amide (compound I, $R^4$=$CH_2CH(CH_3)_2$) were obtained, melting point 202°–203°.

$C_{20}H_{23}F_3N_6O_2$ (436.45) Calculated: C 55.04 H 5.31 F 13.06 N 19.26% Found: C 55.1 R 5.2 F 12.5 N 18.9%

EXAMPLE 75

The cyclization reaction was carried out in the same way and with the same compound II as in Example 74 to form the same compound I (as in Example 74) with a mixture of 3.06 g (7 mmol) of said compound II, 1.2 ml of 33% strength HBr/$CH_3COOH$ solution (~6.7 mmol) and 5.0 ml of formic acid. 0.98 g (32% yield) of compound I ($R^1$=$CH_3$; $R^2$, $R^3$, $R^5$, $R^6$=H; $R^4$=$CH_2CH(CH_3)_2$) was obtained, melting point 202°–203°.

EXAMPLE 76

A mixture of 2.62 g (6 mmol) of the same compound II as in Example 74, and 6.6 ml of propionic acid was stirred at 70° for 2 hours and then worked up as described in Example 5. 1.65 g (63% yield) of the same compound I ($R^1$=$CH_3$; $R^2$, $R^3$, $R^5$, $R^6$=H; $R^4$=$CH_2CH(CH_3)_2$) as in Example 74 were obtained, melting point 202°–203°.

EXAMPLE 77

A mixture of 2.78 g (6 mmol) of a compound II ($R^1$=CH=$CH_2$; $R^2$, $R^3$, $R^5$, $R^6$=H; $R^4$=n-$C_5H_{11}$), 5 ml of propionic acid and 270 mg of oxalic acid was stirred at 60° for 3 hours and then worked up as in Example 5. 1.86 g (67% yield) of pure 4-amino-2-(4-vinyl-2-oxo-1-imidazolidinyl)pyrimidine-5-carboxylic acid N-pentyl-N-(3-trifluoromethylphenyl)amide (compound I, $R^1$=CH=$CH_2$; $R^2$, $R^3$, $R^5$, $R^6$=H; $R^4$=n-$C_5H_{11}$) were obtained, melting point

133°–134°.

$C_{22}H_{25}F_3N_6O_2$ (462.49) Calculated: C 57.13 H 5.45 F 12.32 N 18.17% Found: C 56.6 H 5.1 F 11.6 N 18.1%

EXAMPLE 78

A mixture of 3.04 g (7 mmol) of a compound II ($R^1$, $R^2$=$CH_3$; $R^3$, $R^5$, $R^6$=H; $R^4$=$CH_2CH$=$CH_2$), 0.45 ml (~5.8 mmol) of trifluoroacetic acid and 5.0 ml of glacial acetic acid was stirred at 70° for 2 hours and worked up as described in Example 5. 2.00 g (=65.8% yield) of the compound I ($R^1$, $R^2$=$CH_3$; $R^3$, $R^5$, $R^6$=H; $R^4$=$CH_2CH$=$CH_2$) were obtained, melting point 189°.

EXAMPLE 79

A mixture of 2.63 g (6 mmol) of a compound II ($R^1$=CH=$CH_2$; $R^2$, $R^3$, $R^6$=H; $R^4$=$C_2H_5$; $R^5$=F), 304 mg (4 mmol) of glycolic acid and 5.2 ml of glacial acetic acid was stirred at 60° for 3 hours and then worked up as in Example 5. 1.69 g (64.3% yield) of pure 4-amino-2-(4-vinyl-2-oxo-1-imidazolidinyl)pyrimidine-5-carboxylic acid N-ethyl-N-(2-fluoro-5-trifluoromethylphenyl)amide (compound I, $R^1$=CH=$CH_2$; $R^2$, $R^3$, $R^6$=H; $R^4$=$C_2H_5$; R5=F) were obtained, melting point 240°–241°.

$C_{19}H_{18}F_4N_6O_2$ (438.40) Calculated: C 52.05 H 4.14 F 17.34 N 19.17% Found: C 51.9 H 3.9 F 17.0 N 19.1%

EXAMPLE 80

A mixture of 3.14 g (7 mmol) of a compound II ($R^1$=CH=$CH_2$; $R^2$, $R^3$, $R^5$, $R^6$=H; $R^4$=$CH_2CH(CH_3)_2$), 5 ml of glacial acetic acid and 1.05 g (5.5 mmol) of p-toluenesulfonic acid monohydrate was stirred at 67°–69° for 2.5 hours and then worked up as in Example 5. 1.67 g (53.2% yield) of TLC-pure 4-amino-2-(4-vinyl-2-oxo-1-imidazolidinyl)pyrimidine-5-carboxylic acid N-isobutyl-N-(3-trifluoromethylphenyl)amide were obtained, melting point 85°–186°.

$C_{21}H_{23}F_3N_6O_2$ (448.46) Calculated: C 56.24 H 5.17 F 12.71 N 18.74% Found: C 55.7 H 5.2 F 12.1 N 18.7%

EXAMPLE 81

A mixture of 2.41 g (5 mmol) of a compound II ($R^1$=$CH_3$; $R^2$, $R^3$, $R^5$=H; $R^4$=$CH_3CHCH_2CH(CH_3)_2$; $R^6$=F), 270 mg (3 mmol) of oxalic acid and 4.2 ml of propionic acid was stirred at 70° for 2 hours and then worked up as in Example 5. 1.50 g (62.3% yield) of the compound I ($R^1$=$CH_3$; $R^2$, $R^3$, $R^5$=H ; $R^4$=$CH_3CHCH_2CH(CH_3)_2$; $R^6$=F) were obtained, melting point 135°–137°.

$C_{22}H_{26}F_4N_6O_2$ (482.50) Calculated: C 54.77 H 5.43 F 15.75 N 17.42% Found: C 54.1 H 5.0 F 15.2 N 17.0%

EXAMPLE 82

A solution of 40 g of (85–90% pure) 2-cyano-3-ethoxyacrylic acid N-allyl-N-(3-trifluoromethylphenyl)amide (compound IV: $R^4$=$CH_2CH$=$CH_2$; $R^5$, $R^6$=H; $R^7$=$C_2H_5$) in 82 ml of anhydrous acetonitrile was added dropwise to a stirred suspension of 16.8 g (107.6 mmol) of 1-amidino-4, 4-dimethyl-2-oxoimidazolidine (compound III: $R^1$, $R^2$=$CH_3$; $R^3$=H) in 75 ml of anhydrous acetonitrile at 20°, and the mixture was stirred at 20° for 2 hours and at 20°–23° for 3 hours. Solid separated out during this. The mixture was diluted with 150 ml of ether, left to stand at 4°–6° for 15 hours and then the solid was filtered off with suction and washed with ether. The solid was suspended in 200 ml of water, stirred at room temperature for 30 minutes, filtered off with suction, washed with water and dried in vacuo (160–180 mbar) over $P_4O_{10}$ at room temperature (20°–24°) for 48 hours. 27.8 g (59.5% yield) of 1-cyano-1-[N-allyl-N-(3-trifluoromethylphenyl)carbamoyl]-2-[imino(4,4-dimethyl-2-oxo-1-imidazolidinyl)methylamino]ethene (compound II: $R^1$, $R^2$=$CH_3$; $R^3$, $R^5$, $R^6$=H; $R^4$=$CH_2CH$=$CH_2$) were obtained, melting point 184°–185°.

$C_{20}H_{21}F_3N_6O_2$ (434.44) Calculated: C 55.29 H 4.87 F 13.12 N 19.35% Found: C 54.7 H 4.6 F 12.5 N 18.9%

EXAMPLE 83

A solution of 11.93 g (40 mmol) of 2-cyano-3-ethoxyacrylic acid N-methyl-N-(3-trifluoromethylphenyl)amide (compound IV: $R^4$=$CH_3$; $R^5$, $R^6$=H; $R^7$=$C_2H_5$) in 30 ml of abs. acetonitrile was added dropwise to a stirred suspension of 5.69 g (40 mmol) of 1-amidino-4-methyl-2-oxo-imidazolidine (compound III: $R^1$=$CH_3$; $R^2$, $R^3$=H) in 30 ml of abs acetonitrile at 20°, and the mixture was stirred at 20° for 3 hours. Then 100 ml of ether were added, the mixture was stirred while cooling in ice for 1 hour and subsequently the solid which had separated out was filtered off with suction. The latter was washed with a little cold acetonitrile and with ether and then suspended in 200 ml of water and stirred at room temperature for 30 minutes, and the solid was again filtered off with suction and dried over $P_4O_{10}$ in vacuo (6–8 mbar) for 50 hours. 12.2 g (=77.4% yield) of TLC-pure 1-cyano-1-[N-methyl-N-(3-trifluoromethylphenyl)carbamoyl]-2-[imino(4-methyl-2-oxo-1-imidazolidinyl)methylamino]ethene (compound II: $R^1$, $R^4$=$CH_3$; $R^2$, $R^3$, $R^5$, $R^6$=H) were obtained, melting point 195°–196°.

$C_{17}H_{17}F_3N_6O_2$ (394.37) Calculated: C 51.78 H 4.35 F 14.45 N 21.31% Found: C 52.0 H 4.1 F 14.1 N 21.4%

EXAMPLE 84

In a manner analogous to the description in Examples 82 and 83, a solution of 20 g (about 86% pure, =~5.5 mmol) of a compound IV ($R^4$, $R^7$=$C_2H_5$; $R^5$, $R^6$=H) in 42 ml of abs. acetonitrile was added dropwise to a suspension of 7.82 g (55 mmol) of compound III ($R^1$=$CH_3$; $R^2$, $R^3$=H) in 38 ml of abs. acetonitrile, then stirred and subsequently worked up. 11.3 g (=50.4% yield) of TLC-pure 1-cyano-1-[N-ethyl-N-(3-trifluoromethylphenyl)carbamoyl]-2-[imino(4-methyl-2-oxo-1-imidazolidinyl)methylamino]ethene (compound II: $R^1$=$CH_3$; $R^2$, $R^3$, $R^5$, $R^6$=H; $R^4$=$C_2H_5$) were obtained, melting point 180°–181°.

$C_{18}H_{19}F_3N_6O_2$ (408.40) Calculated: C 52.94 H 4.69 F 13.96 N 20.58% Found: C 52.5 H 4.7 F 12.9 N 21.1%

EXAMPLE 85

A solution of 27.5 g of (80–85% pure) 2-cyano-3-ethoxyacrylic acid N-cyclopropylmethyl-N-(3-trifluoromethylphenyl)amide (compound IV: $R^4$=$CH_2$-◁, $R^5$, $R^6$=H; $R^7$=$C_2H_5$) in 48 ml of abs. dimethoxyethane (DME) was added dropwise to a stirred suspension of 11.0 g (70 mmol) of 1-amidino-4,4-dimethyl-2-oxoimidazolidine in 45 ml of abs. DME at 18°–20°, and the mixture was stirred at 20°–23° for 3.5 hours. The reaction mixture was then evaporated in vacuo at a maximum bath temperature of 25°. The oily residue was dissolved in 200 ml of ether and shaken with 50 ml of 2N HCl. During this, crystals (hydrochloride of the compound II formed ($R^1$, $R^2$=$CH_3$; $R^3$, $R^5$, $R^6$=H; $R^4$=$CH_2$-◁)) separated out. The latter were filtered off with suction and washed with ether and with water. This crystalline substance was then suspended in 150 ml of water and, at 10°–18°, 2N NaOH was added dropwise until the pH was adjusted to 8.7–8.9. The mixture was then stirred while cooling in ice for 1 hour, the solid was filtered off with suction, and the latter was washed with water and dried over $P_2O_5$ in vacuo (6–8 mbar) at 22°–24° for 50 hours. 11.2 g (38.3% yield) of 1-cyano-1-[N-cyclopropylmethyl-N-(3-trifluoromethylphenyl)carbamoyl]-2-[imino(4,4-dimethyl-2-oxo-1-imidazolidinyl)methylamino]ethene (compound II: $R^1$, $R^2$=$CH_3$; $R^3$, $R^5$, $R^6$=H; $R^4$=$CH_2$-◁) were obtained, melting point 180°–181° (decomposition).

$C_{21}H_{23}F_3N_6O_2$ (448.46) Calculated: C 56.24 H 5.17 F 12.71 N 18.74% Found: C 56.4 H 5.1 F 12.4 N 19.1%

EXAMPLE 86

0.5 ml of 2N HCl was added to a suspension of 449 mg (1 mmol) of the compound II obtained as in Example 85 in 2.5 ml of water at room temperature, and the mixture was stirred at room temperature for 10 minutes and while cooling in ice for 40 minutes and then filtered with suction. The crystals were dried over $P_4O_{10}$ in vacuo (6–8 mbar) at 23°–25° for 28 hours. 0.46 g (94.9% yield) of 1-cyano-1-[N-cyclopropylmethyl-N-(3-trifluoromethylphenyl)carbamoyl]-2-[imino(4,4-dimethyl-2-oxo-1-imidazolidinyl)methylamino]ethene hydrochloride was obtained, melting point 179°–180°.

$C_{21}H_{24}ClF_3N_6O_2$ (484.93) Calculated: Cl•7.31% Found: Cl•7.4%

EXAMPLE 87

A solution of 8.2 g of (unpurified, about 90% pure) 2-cyano-3-ethoxyacrylic acid N-isopropyl-N-(3-trifluoromethylphenyl)amide (compound IV: $R^4$=$CH(CH_3)_2$; $R^5$, $R^6$=H; $R^7$=$C_2H_5$) in 20 ml of abs. DME was added dropwise to a suspension of 3.91 g (25 mmol) of 1-amidino-4,4-dimethyl-2-oxoimidazolidine in 16 ml of abs. DME at 20°, and the mixture was stirred at 22°–24° for 4.5 hours. The mixture was then evaporated in vacuo at a maximum bath temperature of 25°. The oily residue was taken up in 250 ml of ether and extracted six times with 25 ml of water each time. The etherial solution was then dried over $MgSO_4$, filtered and evaporated in vacuo (<26°). The residue (12.7 g) was partially crystalline. The latter was taken up in 40 ml of ether, 2 ml of pentane were added, the mixture was left to stand at 4°–6° for 2 days and subsequently the crystals were filtered off with suction. Drying (over $P_4O_{10}$ at 20°–24°, 6–8 mbar, 48 hours) resulted in 5.12 g (=47% yield) of TLC-pure compound II ($R^1$, $R^2$=$CH_3$; $R^3$, $R^5$, $R^6$=H; $R^4$=$CH(CH_3)_2$), melting point 121°–122° C.

$C_{20}H_{23}F_3N_6O_2$ (436.45) Calculated: C 55.04 H 5.31 F 13.06 N 19.26% Found: C 54.9 H 5.6 F 12.4 N 18.5%

EXAMPLE 88

In the same way as described in Example 86, 1 mmol (437 mg) of the compound II prepared as in Example 87 was converted into the hydrochloride. 400 mg (84.6% yield) of 1-cyano-1-[N-isopropyl-N-(3-trifluoromethylphenyl)carbamoyl]-2-[imino(4,4-dimethyl-2-oxo-1-imidazolidinyl)methylamino]ethene hydrochloride were obtained, melting point 258°–260°.

$C_{20}H_{24}ClF_3N_6O_2$ (472.92) Calculated: Cl•7.50% Found: Cl•7.4%

EXAMPLE 89

In the same way as described in Example 86, 1 mmol (479 mg) of the compound II prepared as in Example 97 was converted into the hydrochloride. 1.02 g (99%) of 1-cyano-1-[N-(1,3-dimethyl-1-butyl)-N-(3-trifluoromethylphenyl)carbamyl]-2-[imino(4,4 -dimethyl-2-oxo-1-imidazolidinyl)methylamino]ethene hydrochloride were obtained, melting point 255°–256°.

$C_{23}H_{30}ClF_3N_6O_2$ (5 15.00) Calculated: C 53.64 H 5.87 Cl•6.88 F 11.07 N 16.32% Found: C 53.4 H 5.9 Cl•6.4 F 10.6 N 16.1%

The compounds II (Examples 90–112) listed in the following Table 5 were prepared by the procedures described in Examples 82–84, 85 and 87, which differ in particular in the procedure for the working up. For each of the individual compounds in Table 5, reference is made to the Example according to which the compound II was prepared.

TABLE 5

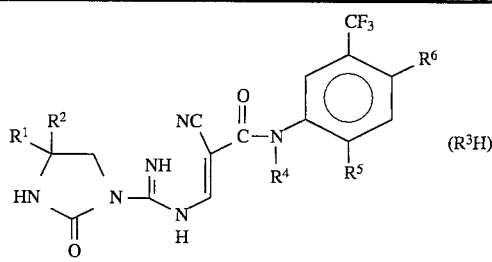

(R³H)    II

| Ex. No. | $R^1$ | $R^2$ | $R^4$ | $R^5$ | $R^6$ | m.p. [°C.] | Calc. C | H | F | N | Found C | H | F | N | Obtained as in Example |
|---|---|---|---|---|---|---|---|---|---|---|---|---|---|---|---|
| 90 | $CH_3$ | $CH_3$ | $C_2H_5$ | H | H | 176–77 | 54.02 | 5.01 | 13.49 | 19.90 | 54.3 | 5.0 | 12.5 | 20.2 | 82–84 |
| 91 | $CH_3$ | $CH_3$ | $C_2H_5$ | F | H | 213–14 | 51.82 | 4.58 | 17.26 | 19.08 | 51.9 | 4.9 | 16.4 | 19.1 | 82–84 |
| 92 | $CH_3$ | $CH_3$ | $CH(CH_3)_2$ | H | F | 197–98 | 52.86 | 4.88 | 16.72 | 18.49 | 53.1 | 4.6 | 15.9 | 18.3 | 82–84 |
| 93 | $CH_3$ | $CH_3$ | $C_4H_9$ | H | H | 191–92 | 55.99 | 5.59 | 12.65 | 18.66 | 56.0 | 5.5 | 12.5 | 18.9 | 85 |
| 94 | $CH_3$ | $CH_3$ | $H_3CCHC_2H_5$ | H | H | 178– | 55.99 | 5.59 | 12.65 | 18.66 | 56.0 | 5.4 | 12.7 | 18.5 | 85 |

TABLE 5-continued

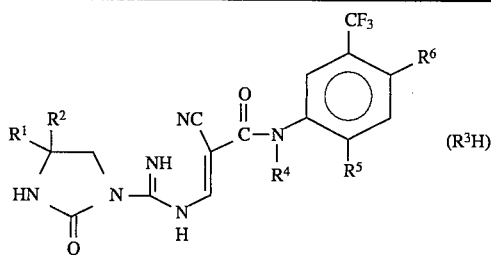

| Ex. No. | R¹ | R² | R⁴ | R⁵ | R⁶ | m.p. [°C.] | Calc. C | H | F | N | Found C | H | F | N | Obtained as in Example |
|---|---|---|---|---|---|---|---|---|---|---|---|---|---|---|---|
| 95 | $CH_3$ | $CH_3$ | $C_5H_{11}$ | H | H | 80 173–74 | 56.89 | 5.86 | 12.27 | 18.09 | | | | | 82–84 |
| 96 | $CH_3$ | $CH_3$ | $CH_2C(CH_3)_3$ | H | H | 124–26 | 56.89 | 5.86 | 12.27 | 18.09 | 57.2 | 5.9 | 11.8 | 18.2 | 82–84 |
| 97 | $CH_3$ | $CH_3$ | $H_3CCHCH_2CH(CH_3)_2$ | H | H | 141–43 | 57.73 | 6.11 | 11.91 | 17.56 | 56.8 | 6.0 | 11.6 | 17.2 | 85 |
| 98 | $CH_3$ | $CH_3$ | $H_3CCHCH_2CH(CH_3)_2$ | H | F | 156–57 | 55.64 | 5.68 | 15.31 | 16.93 | 55.3 | 5.4 | 15.6 | 16.9 | 85 |
| 99 | $CH_3$ | $CH_3$ | $CH_2CH=CH_2$ | H | H | 184–85 | 55.29 | 4.87 | 13.12 | 19.35 | | | | | 82–84 |
| 100 | $CH_3$ | $CH_3$ | $H_3CCH(CH_2)_2CH=C(CH_3)_2$ | H | H | 116–17 | 59.51 | 6.19 | 11.30 | 16.66 | 58.5 | 6.1 | 10.8 | 16.6 | 85 |
| 101 | $CH_3$ | $CH_3$ | cyclopentyl | H | H | 185–86 | 57.13 | 5.45 | 12.32 | 18.17 | 56.9 | 5.4 | 11.3 | 18.0 | 87 |
| 102 | $CH_3$ | $CH_3$ | $CH_3$-cyclopropyl | F | H | 210–11 | 54.07 | 4.75 | 16.29 | 18.02 | 54.2 | 4.7 | 15.9 | 17.7 | 82–84 |
| 103 | H | H | $CH_3$ | H | H | 195–96 | 50.53 | 3.98 | 14.99 | 22.10 | 50.1 | 4.0 | 13.4 | 23.7 | 82–84 |
| 104 | H | H | $C_4H_9$ | H | H | 213–14 | 54.02 | 5.01 | 13.49 | 19.90 | 53.5 | 5.0 | 12.8 | 19.9 | 82–84 |
| 105 | $CH_3$ | H | $CH_3$ | H | H | 195–96 | 51.78 | 4.35 | 14.45 | 21.31 | 52.0 | 4.1 | 14.1 | 21.4 | 82–84 |
| 106 | $CH_3$ | H | $CH_2CH(CH_3)_2$ | H | H | 152–53 | 55.04 | 5.31 | 13.06 | 19.26 | 54.1 | 4.9 | 12.3 | 18.7 | 82–85 |
| 107 | $CH_3$ | H | $H_3CCHCH_2CH(CH_3)_2$ | H | F | 173–74 | 54.77 | 5.43 | 15.75 | 17.42 | | | | | 85 |
| 108 | $CH_3$ | H | cyclopentyl | H | H | 166–67 | 56.24 | 5.17 | 12.71 | 18.74 | 54.2 | 5.0 | 12.0 | 17.9 | 85 |
| 109 | $CH=CH_2$ | H | $CH_3$ | H | H | 192–93 | 53.20 | 4.22 | 14.03 | 20.68 | 53.4 | 4.0 | 13.4 | 20.3 | 82–84 |
| 110 | $CH=CH_2$ | H | $C_2H_5$ | F | H | 202–03 | 52.05 | 4.14 | 17.34 | 19.17 | 51.8 | 4.3 | | 19.4 | 82–84 |
| 111 | $CH=CH_2$ | H | $CH_2CH(CH_3)_2$ | H | H | 175–76 | 56.24 | 5.17 | 12.71 | 18.74 | 55.8 | 5.0 | | 18.9 | 85 |
| 112 | $CH=CH_2$ | H | $C_5H_{11}$ | H | H | 146–47 | 57.13 | 5.45 | 12.32 | 18.17 | 57.0 | 5.7 | | 18.5 | 82–84 |

EXAMPLE 113

0.57 ml of a 6.17 molar solution of HCl in ether was added to a solution of 1.315 g (3 mmol) of the compound I ($R^1$=CH=$CH_2$; $R^2$, $R^3$, $R^6$=H; $R^4$=$C_2H_5$; $R^5$=F) prepared as in Example 79 in 10 ml of acetone at room temperature. The resulting suspension was stirred while cooling in ice for 1.5 hours. The crystals were then filtered off with suction, washed with acetone and ether and dried in vacuo (5–8 mbar) at 100° for 15 hours. 1.40 g (=98.3% yield) of pure 4-amino-2-(4-vinyl-2-oxo-1-imidazolidinyl)pyrimidine-5-carboxylic acid N-methyl-N-(2-fluoro-5-trifluoromethylphenyl)amide hydrochloride were obtained, melting point 259°–260° C. (decomposition).

$C_{19}H_{19}ClF_4N_6O_2$ (474.87) Calculated: Cl•7.47% Found: Cl•7.4%

The hydrochlorides of compounds I listed in the following Table 6 (Examples 114 to 117) were prepared as in Example 113 and Example 6.

TABLE 6

Examples 114–117

| Example No. | Hydrochloride of compound I of Example | m.p. [°C.] | Calculated Cl⁻ % | Found Cl⁻ % |
|---|---|---|---|---|
| 114 | 74–76 | 276–77 | 7.50 | 7.7 |
| 115 | 81 | 284–85 | 6.83 | 6.8 |
| 116 | 80 | 269–70 | 7.31 | 7.5 |
| 117 | 77 | 247–48 | 7.11 | 7.2 |

EXAMPLE 118

A mixture of 2.80 g (6.41 mmol) of a compound II ($R^1$, $R^2=C_2H_5$; $R^3$, $R^5$, $R^6=H$; $R^4=CH_3$), 210 mg of anhydrous oxalic acid and 4.75 ml of glacial acetic acid was stirred at 70° for 2.5 hours, a solution being produced after 20 min. It was then evaporated in vacuo. The residue was taken up in 70 ml of $CH_2Cl_2$ and extracted three times in succession with 20 ml of N NaOH each time and then twice with 20 ml of water each time. The $CH_2Cl_2$ solution was dried with $MgSO_4$, filtered and evaporated in vacuo. The residue was taken up in about 15 ml of ether, whereupon crystallization occurred. The crystalline product was filtered off with suction and washed with ether and dried in vacuo at 100° for 17 hours. 1.81 g (=64.6% yield) of pure 4-amino-2-(4,4-diethyl-2-oxo-1-imidazolidinyl)pyrimidine-5-carboxylic acid N-methyl-N-(3-trifluoromethylphenyl)amide were obtained, melting point 185°–187°. $C_{20}H_{23}F_3N_6O_2$ (436.45) Calculated: C 55.04 H 5.31 N 19.26% Found: C 54.8 H 5.2 N 19.2

EXAMPLE 119

3.60 g (8.25 mmol) of the compound I ($R^1$, $R^2=C_2H_5$; $R^3$, $R^5$, $R^6=H$; $R^4=CH_3$) prepared in Example 118 were converted into the hydrochloride by the procedure described in Example 6. 3.42 g (=87.7 % yield) of pure 4-amino-2-(4,4-diethyl-2-oxo-1-imidazolidinyl)pyrimidine-5-carboxylic acid N-methyl-N-(3-trifluoromethylphenyl)amide hydrochloride were obtained, melting point 196°–197°.

$C_{20}H_{24}ClF_3N_6O_2$ (472.92) Calculated: C 50.80 H 5.12 Cl·7.50 F 12.05 N 17.77% Found: C 50.9 H 4.9 Cl·7.4 F 11.6 N 17.7%

EXAMPLE 120

Starting from 6.58 g (24.8 mmol) of 1-amidino-4,4-diethyl-2-oxoimidazolidine hydrobromide (comp. III: $R^1$, $R^2=C_2H_5$; $R^3=H$ as hydrobromide) and 3.87 g (26.1 mmol) of diazabicycloundecene (DBU) as auxiliary base and 7.40 g (24.8 mmol) of a compound IV ($R^4=CH_3$; $R^5$, $R^6=H$; $R^7=C_3H_5$) by the procedure described in Examples 82–84, 3.94 g (=36.4% yield) of pure 1-cyano-1-[N-methyl-N-(3-trifluoromethylphenyl)carbamoyl]-2-[imino(4,4-diethyl-2-oxo-1-imidazolidinyl)methylamino]ethene (comp. II: $R^1$, $R^2=C_2H_5$; $R^3$, $R^5$, $R^6=H$; $R^4=CH_3$) were obtained, melting point 184°–87°.

$C_{20}H_{23}F_3N_6O_2$ (436.45) Calculated: C 55.04 H 5.31N 19.26% Found: C 55.5 H 4.9 N 19.5%

EXAMPLE 121

As in Example 118 and starting from 4.52 g (10 mmol) of a compound II ($R^1$, $R^2=CH_3$; $R^3$, $R^5$, $R^6=H$; $R^4=CH_3OCH_2CH_2$), 360 mg of anhydrous oxalic acid and 7 ml of glacial acetic acid, 2.65 g (=58.6% yield) of pure 4-amino-2-(4,4-dimethyl-2-oxo-1-imidazolidinyl)-pyrimidine-5-carboxylic acid N-(2-methoxyethyl)-N-(3-trifluoromethylphenyl)amide were obtained, melting point 192°–93°.

$C_{20}H_{23}F_3N_6O_3$ (452.45) Calculated: C 53.09 H 5.12 N 18.58% Found: C 52.8 H 5.0 N 18.8%

The compound II ($R^1$, $R^2=CH_3$; $R^3$, $R^5$, $R^6=H$; $R^4=CH_3OCH_2CH_2$) required as starting material was prepared by the procedure described in Examples 82–84 starting from the corresponding compounds III ($R^1$, $R^2=CH_3$; $R^3=H$) and IV ($R^4=CH_3OCH_2CH_2$; $R^5$, $R^6=H$; $R^7=C_2H_5$); it has a melting point of 170°–71°.

EXAMPLE 122

2.51 g (5.6 mmol) of the compound I ($R^1$, $R^2=CH_3$; $R^3$, $R^5$, $R^6=H$; $R^4=CH_3OCH_2CH_2$) prepared in Example 121 were converted into the hydrochloride by the procedure described in Example 6. 2.70 g (=~100% yield) of pure 4-amino-2-(4,4-dimethyl-2-oxo-1-imidazolidinyl)pyrimidine- 5-carboxylic acid N-(2-methoxyethyl)-N-(3-trifluoromethylphenyl)amide hydrochloride were obtained, melting point 181°–82°.

$C_{20}H_{24}ClF_3N_6O_3$ (488.92) Calculated: C 49.13 H 4.95 Cl·7.25 F 11.66 N 17.19% Found: C 48.9 H 4.8 Cl·7.3 F 11.6 N 17.0%

EXAMPLE 123

Preparation of a film-coated tablet of the composition specified below:

| Ingredients (per tablet) | | Weight (mg) |
|---|---|---|
| 1. | Compound I of Example 2 | 100 |
| 2. | Lactose | 35 |
| 3. | Corn starch | 20 |
| 4. | Microcrystalline cellulose | 10 |
| 5. | Starch sodium glycolate | 8 |
| 6. | Silicon dioxide | 5 |
| 7. | Magnesium stearate | 2 |
| 8. | Film coating | 10 |
| | Total weight | 190 | a) Substances 1.–4. are mixed, compacted and passed through a Frewitt screen (mesh width 1.0 mm).
b) The granules from a) are dusted with substances 5.–7. and compressed.
c) The tablets from b) are coated with aqueous film coating.

EXAMPLE 124

Preparation of a film-coated tablet of the composition specified below

| Ingredients (per tablet) | | Weight (mg) |
|---|---|---|
| 1. | Compound I of Example 12 | 100 |
| 2. | Lactose | 11 |
| 3. | Hydroxypropylmethylcellulose | 60 |
| 4. | Microcrystalline cellulose | 7 |
| 5. | Magnesium stearate | 2 |
| 6. | Film coating | 10 |
| | Total weight | 190 | a) Substances 1.–4. are mixed, compacted and passed through a Frewitt screen (mesh width 1.0 mm).
b) The granules from a) are dusted with substance 5. and compressed.
c) The tablets from b) are coated with aqueous film coating.

This type of tablet is a formulation with delayed release of active substance.

We claim:

1. A compound which is 4-amino-2-(4,4-dimethyl-2-oxo-1-imidazolidinyl)pyrimidine-5-carboxylic acid N-ethyl-N-(3-trifluoromethylphenyl)amide of the formula

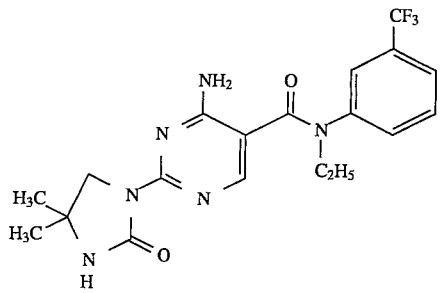

or the physiologically tolerated acid addition salts thereof.

2. The compound of claim 1 wherein the physiologically tolerated acid addition salt is selected from the group consisting of the hydrochloride, the hydrosulfate and the sulfate thereof.

3. A process for the preparation of 4-amino-2-(4,4-dimethyl-2-oxo-1-imidazololidinyl)pyrimidine-5-carboxylic acid N-ethyl-N-(3-trifluoromethylphenyl)amide of the formula

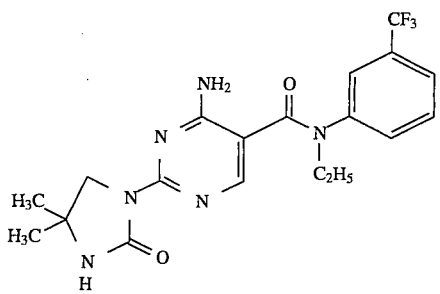

or a salt thereof which comprises maintaining 1-cyano-1-[N-ethyl-N-(3trifluoromethylphenyl)carbamoyl]-2-[imino(4,4-dimethyl-2-oxo-1-imidazolidinyl)methylamino]ethene of the formula

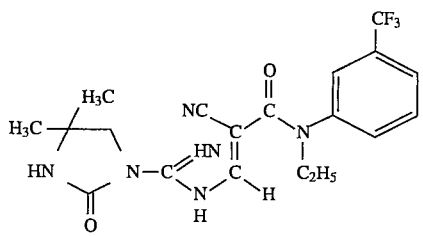

or a salt thereof at a temperature of about 0° C. to about 240° C.

4. The process of claim 3 wherein a solvent is employed.

5. A pharmaceutical composition comprising 4-amino-2-(4,4-dimethyl-2-oxo- 1-imidazolidinyl)pyrimidine-5-carboxylic acid N-ethyl-N-(3-trifluoromethylphenyl)amide of the formula

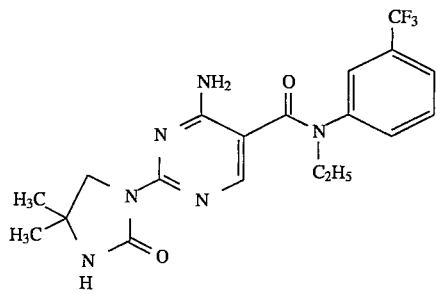

or the physiologically tolerated acid addition salts thereof according to claim 1 and a pharmaceutically acceptable carrier therefor.

6. A method of treating lipid metabolism disorders in a mammal requiring lipid metabolism disorder treatment comprising administering to a mammal a lipid metabolism disorder treatment effective amount of 4-amino-2-(4,4-dimethyl-2-oxo-1-imidazolidinyl)pyrimidine-5-carboxylic acid N-ethyl-N-(3-trifluoromethylphenyl)amide of the formula

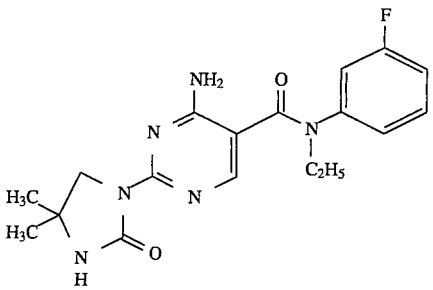

or the physiologically tolerated acid addition salts thereof according to claim 1.

7. A method according to claim 6 wherein the lipid metabolism disorder treatment involves stimulation of the hepatic LDL receptor.

* * * * *